(12) United States Patent
Werth

(10) Patent No.: US 7,357,425 B2
(45) Date of Patent: Apr. 15, 2008

(54) BARB CLAMP

(75) Inventor: Albert A. Werth, Kewadin, MI (US)

(73) Assignee: Twins Bay Medical, Inc., Williamsburg, MI (US)

( * ) Notice: Subject to any disclaimer, the term of this patent is extended or adjusted under 35 U.S.C. 154(b) by 0 days.

(21) Appl. No.: 10/918,240

(22) Filed: Aug. 13, 2004

(65) Prior Publication Data

US 2005/0012332 A1    Jan. 20, 2005

Related U.S. Application Data

(62) Division of application No. 10/100,519, filed on Mar. 18, 2002, now Pat. No. 6,796,586.

(60) Provisional application No. 60/337,363, filed on Dec. 5, 2001, provisional application No. 60/334,918, filed on Oct. 31, 2001, provisional application No. 60/304,014, filed on Jul. 9, 2001.

(51) Int. Cl.
*F16L 33/00* (2006.01)

(52) U.S. Cl. ............... 285/242; 285/419; 285/331; 138/166

(58) Field of Classification Search ........... 285/331, 285/419, 373, 242; 138/166, 167
See application file for complete search history.

(56) References Cited

U.S. PATENT DOCUMENTS

| | | |
|---|---|---|
| 1,390,564 A | 9/1921 | Knorr |
| 2,868,564 A | 1/1959 | Arras |
| 4,564,222 A | 1/1986 | Loker et al. |
| 4,632,435 A | 12/1986 | Polyak |
| 4,723,948 A | 2/1988 | Clark et al. |
| 4,796,856 A | 1/1989 | Munini |
| 4,880,414 A | 11/1989 | Whipple |
| 4,890,866 A | 1/1990 | Arp |
| 4,955,574 A * | 9/1990 | Freier .................. 248/316.5 |
| 5,074,500 A | 12/1991 | Loebbert |
| 5,240,289 A | 8/1993 | Göttling et al. |
| 5,275,447 A | 1/1994 | McNab |
| 5,352,855 A * | 10/1994 | Potter .................. 174/135 |
| 5,584,513 A | 12/1996 | Sweeny et al. |
| 5,882,047 A | 3/1999 | Ostrander et al. |
| 5,909,902 A | 6/1999 | Seabra |

(Continued)

FOREIGN PATENT DOCUMENTS

WO    WO 98/13637    4/1998

*Primary Examiner*—Aaron Dunwoody
(74) *Attorney, Agent, or Firm*—Young Basile

(57) ABSTRACT

A barb clamp provides a leakproof connection of a flexible tube in a barbed fitting. The barb clamp includes a collet and sleeve. The barb fitting is configured to fit snugly within the tube. The collet is slid over the tube. Shelves on the interior surface of the collet fit tightly around the tube and under an expanded portion of the barb fitting. The sleeve is then slid over the collet. As the sleeve moves over the collet, tangs on the collet are pushed radially inwardly into the tube and barb fitting. The sleeve is moved over the collet until an annular projection on the interior surface of the sleeve sits within an annular groove of the collet. Radial ledges on the exterior surface of the collet provide a stop and lock to prevent the annular projection on the sleeve to move out of the annular groove of the collet.

6 Claims, 18 Drawing Sheets

U.S. PATENT DOCUMENTS

| | | |
|---|---|---|
| 5,984,378 A | 11/1999 | Ostrander et al. |
| 6,155,610 A | 12/2000 | Godeau et al. |
| 6,170,887 B1 | 1/2001 | Salomon-Bahls et al. |
| 6,357,196 B1 * | 3/2002 | McCombs ................ 52/736.2 |

* cited by examiner

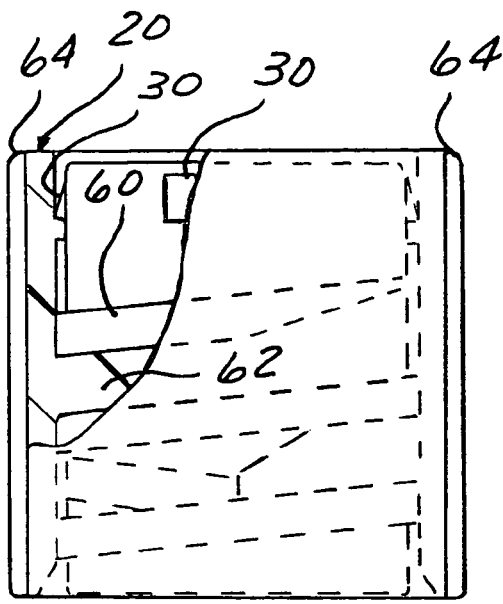
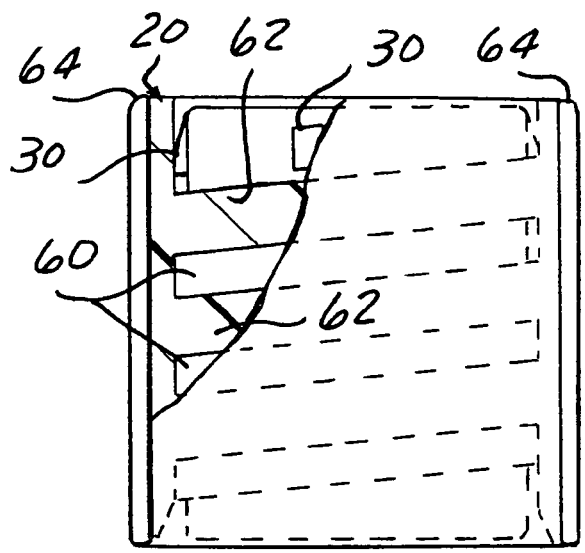
FIG. 19        FIG. 20
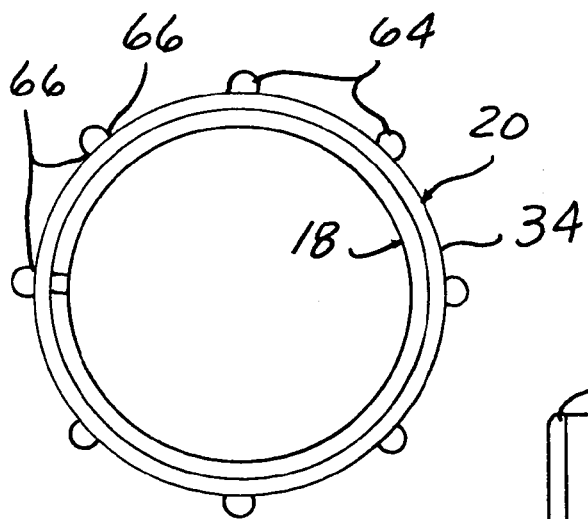
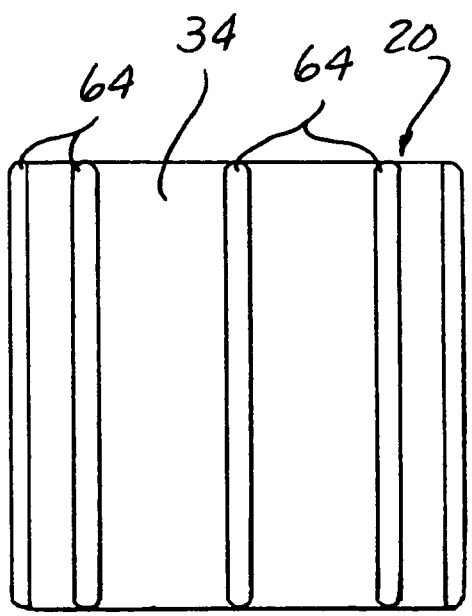
FIG. 21        FIG. 22

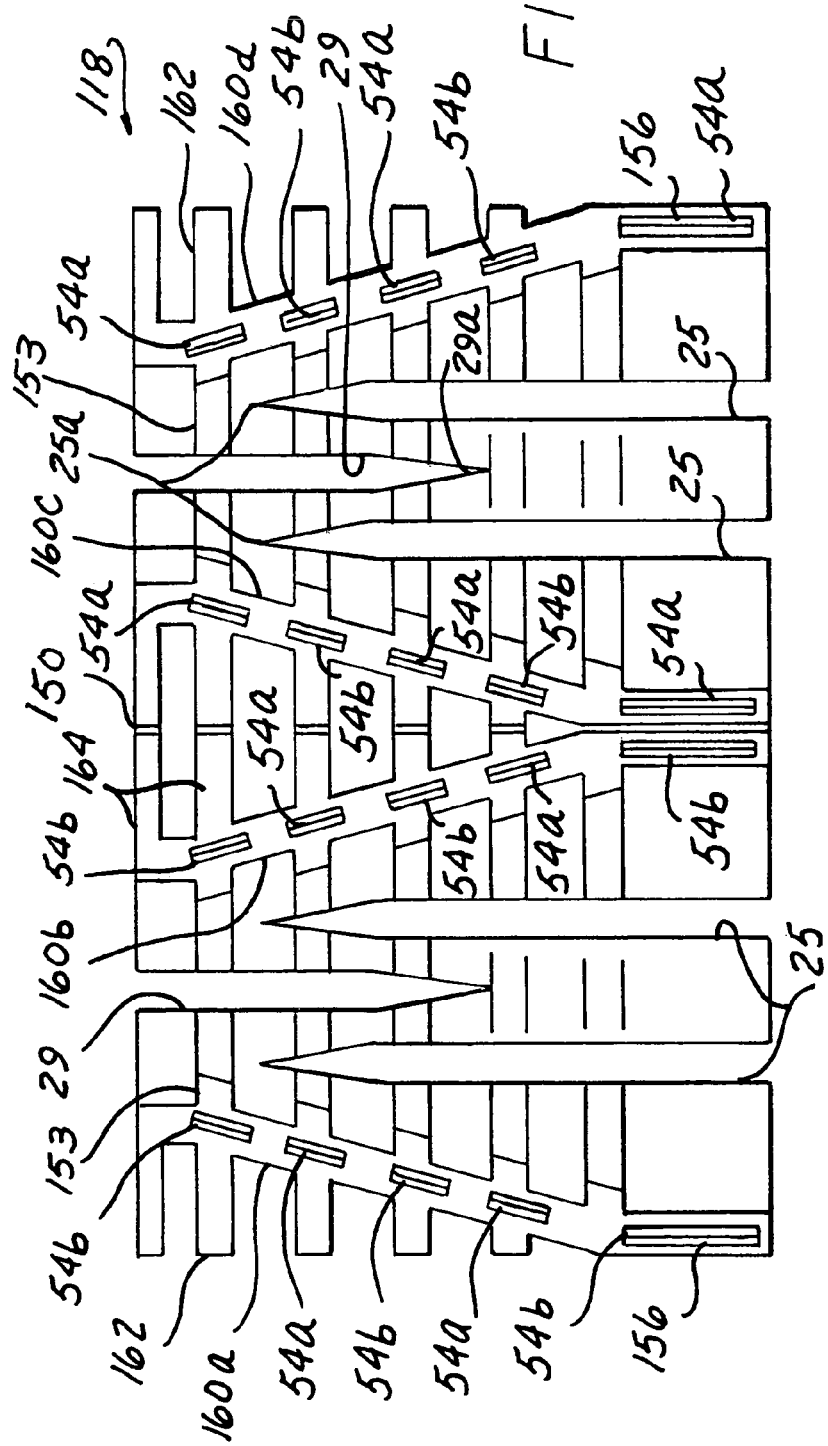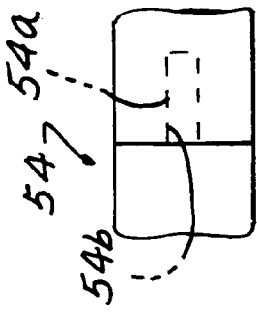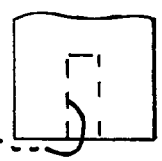

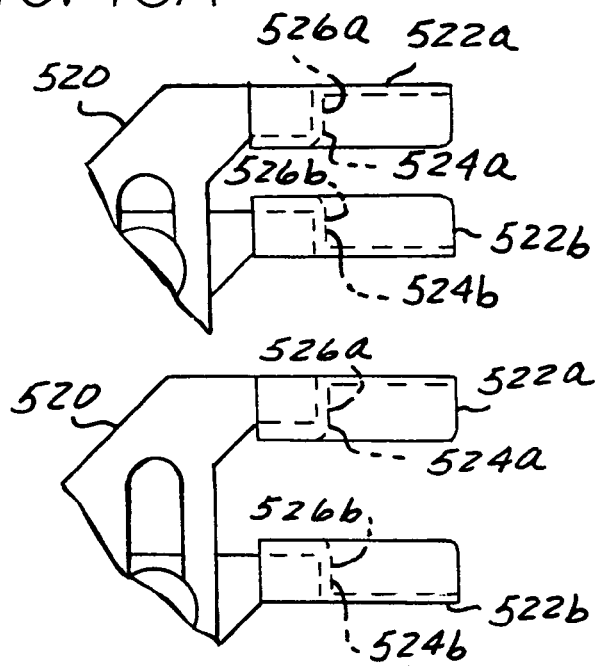
FIG. 43A
FIG. 43B
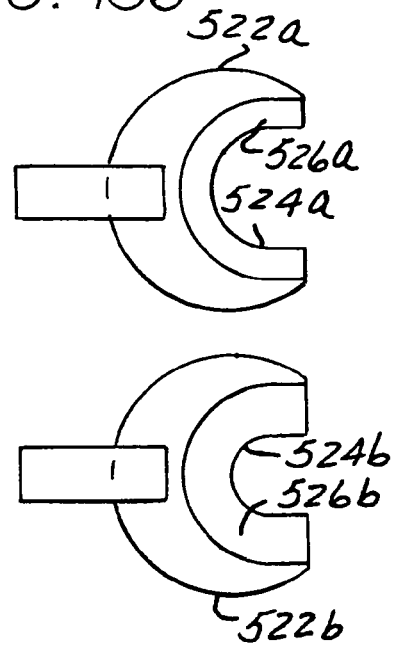
FIG. 43C
FIG. 43D
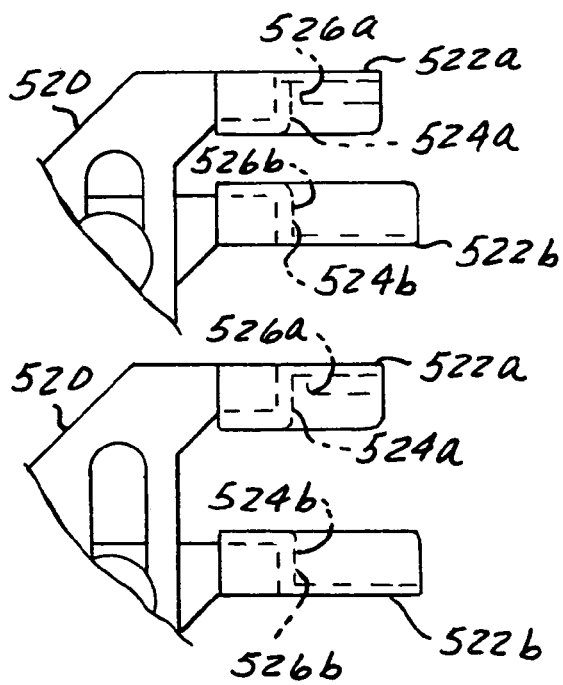
FIG. 44A
FIG. 44B
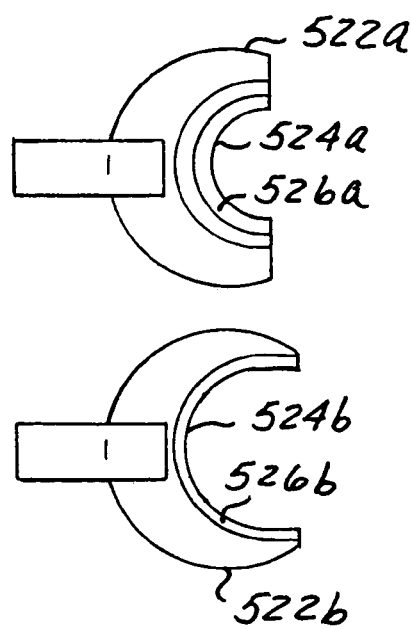
FIG. 44C
FIG. 44D

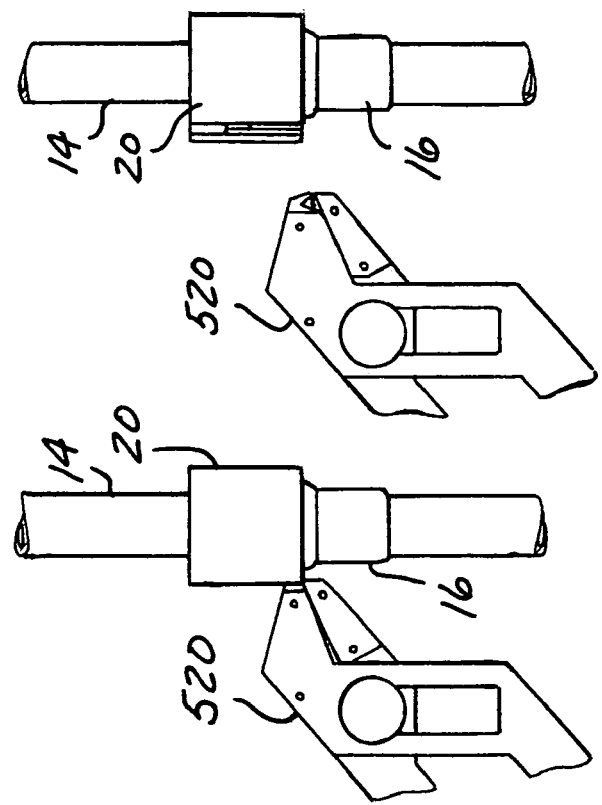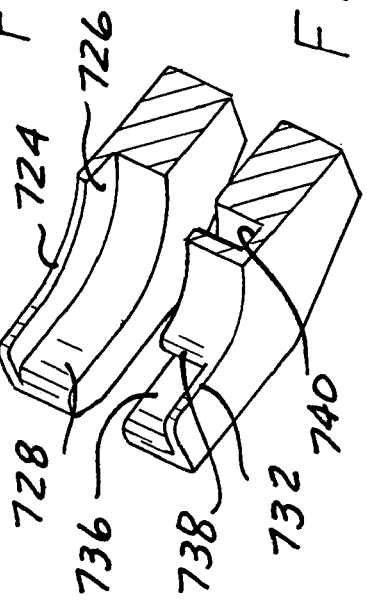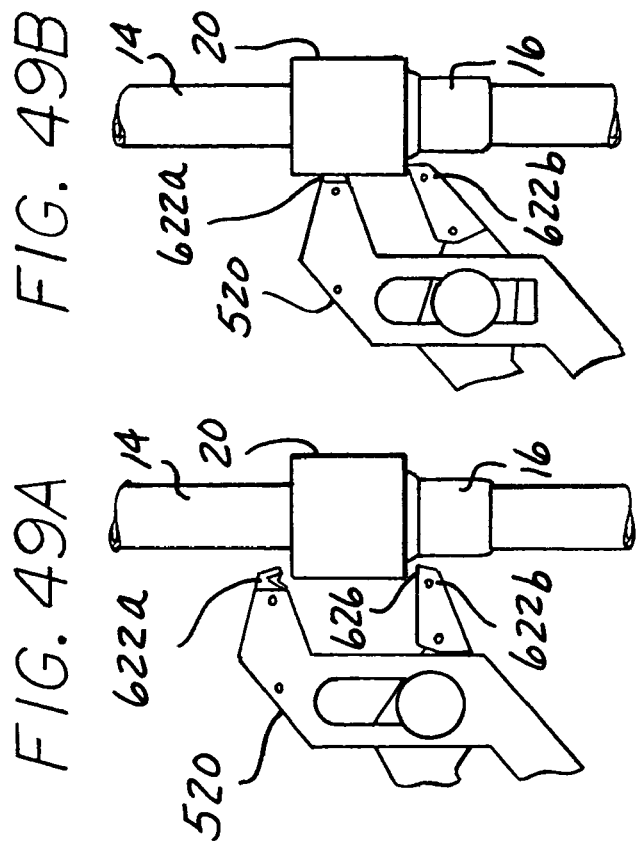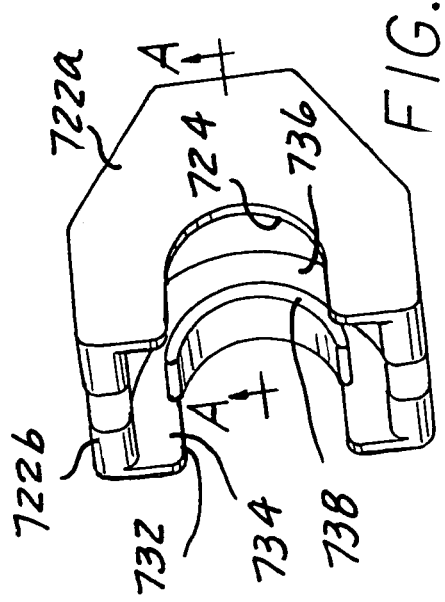

BARB CLAMP

This application is a divisional of U.S. Ser. No. 10/100, 519 filed Mar. 18, 2002, now U.S. Pat. No. 6,796,586, issued on Sep. 28, 2004 which claims priority of the following U.S. provisional applications: Ser. No. 60/304,014, filed on Jul. 9, 2001; Ser. No. 60/334,918, filed on Oct. 31, 2001; and Ser. No. 60/337,363, filed on Dec. 5, 2001.

FIELD OF THE INVENTION

The present invention relates to a fastening device for a tubular body.

BACKGROUND OF THE INVENTION

The transfer of fluid through flexible tubing is widely used in various environments. Ultimately, the flexible tubing is connected to the source of the gaseous or liquid fluid, the delivery site of the fluid, or to another flexible tubing. At the ends of the flexible tubing, it is necessary to provide a secure and leak proof connections. Although these requirements are necessary in all environments using flexible tubing, it is critical in the medical and pharmaceutical fields. In the medical and pharmaceutical fields flexible tubing and associated connections are used for luer fittings, quick connects, or sanitary fittings such as used in blood pumps, oxygen concentrators, sleep apnea equipment, medical transport containers, IV bags, etc. Currently the flexible tubing in these areas use cable ties. In the automotive and other industrial environments, the flexible tubing is connected to a barb fitting by hose clamps. Both of these means of connection demonstrate poor pull off strength and provides an inherent leak path.

SUMMARY OF THE INVENTION

The present invention addresses the aforementioned concerns. The present invention is a barb clamp used for joining a flexible tube to a barbed fitting. In one aspect of the invention the barb clamp includes a barb fitting having one end attached to a device and a second end insertable into the flexible tube. The barb clamp includes a collet engageable over the end of the barb fitting and flexible tube, and further includes a sleeve having a through center aperture for receiving the collet.

In another aspect of the invention the collet has a resilient means for radially contracting around the tube for forming a tight seal.

In another aspect of the invention, the collet has an exterior surface and an annular groove in the exterior surface for receiving an annular projection on the interior surface of the sleeve.

Further, in another aspect of the invention, the collet has one side that is openable to form a pair of clam shell halves.

In yet another aspect of the invention, the sleeve and collet may be combined in a unitary piece.

Further in other aspects of the invention, tools are provided for assembling and disassembling the barb fitting.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

The description herein makes reference to the accompanying drawings wherein like reference numerals refer to like parts throughout the several views, and wherein:

FIG. 19 is a sectional view of the collet in FIG. 17 with a sleeve having a single thread;

FIG. 20 is a sectional view of the collet in FIG. 17 with a sleeve having thread along its axial length;

FIG. 21 is a top view of the sleeve and collet in FIG. 20;

FIG. 22 is a side elevational view of the sleeve in FIG. 21;

FIG. 23a is an elevational view of a seventh embodiment of the collet shown in the open position;

FIG. 23b is an elevational view of a male component of a wedge on the collet shown in FIG. 23a;

FIG. 23c is an elevational view of a female component of the wedge on the collet shown in FIG. 23a;

FIG. 23d is an elevational view of the wedge shown in FIG. 23a when the male and female components are connected to form an interlock;

FIG. 23e is an elevational view of an alternative male component of the wedge on the collet shown in FIG. 23a;

FIG. 23f is an elevational view of an alternative female component of the wedge on the collet shown in FIG. 23a;

FIG. 23g is an elevational view of the wedge shown in FIG. 23a when the male and female components in FIGS. 23e and 23f are connected to form the interlock;

FIGS. 43a-d show a second configuration of the jaws in FIG. 41 in a closed position, open position, bottom view of the upper jaw, and top view of the lower jaw, respectively;

FIGS. 44a-d show a third configuration of the jaws in FIG. 41 in a closed position, open position, bottom view of the upper jaw, and top view of the lower jaw, respectively;

FIG. 49a-d shows a sleeve slitter in the process of cutting a slit in a sleeve for removal;

FIG. 50a shows a perspective view of upper and lower jaws used to disassemble the barb clamp; and FIG. 50b is a sectional view of the upper and lower jaws taken along lines A-A of FIG. 50a.

DETAILED DESCRIPTION OF THE PREFERRED EMBODIMENT

Figure 1:
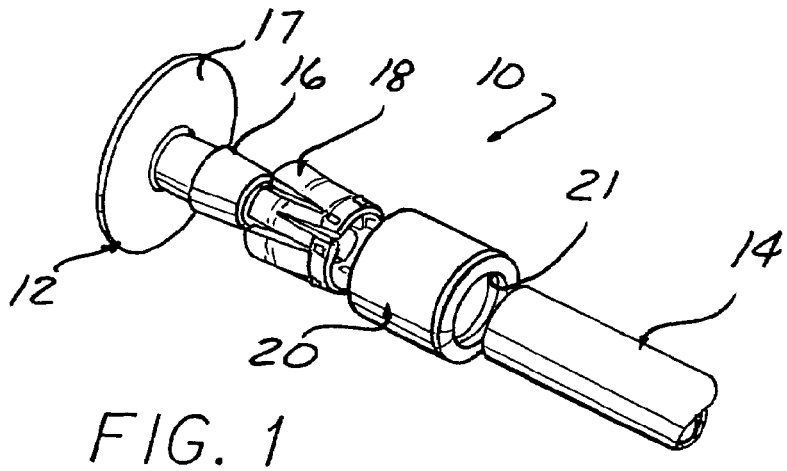
FIG. 1 is a perspective view of the first embodiment of the barb clamp of the present invention before engagement.
Figure 2:
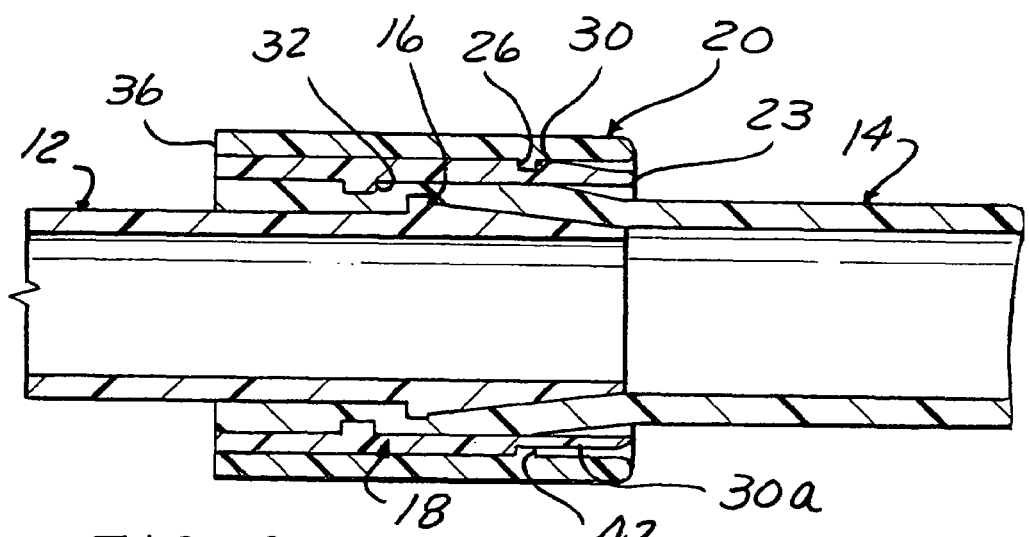
FIG. 2 is a sectional view of the first embodiment of the barb clamp as engaged over a tube.

FIGS. 1 and 2 show the barb clamp connector 10 of the first embodiment of the present invention for coupling a barbed fitting 12 and a flexible tube 14. In the medical or pharmaceutical environment, the barbed fitting 12 is generally made of a non-metal material which allows it to be heat welded to a propylene or ethylene medical or pharmaceutical bag. The barb fitting 12 may encompass different configurations but will generally include an expanded or barbed end 16 for a 360° radial compression connection into the flexible tube 14. If the barb clamp is to be used in a medical or pharmaceutical environment, the barb fitting 12 is preferably made of an FDA (Food and Drug Administration) approved polypropylene, silicon, TPE, TPR, etc. However, in the automotive or other industrial environment, the barb fitting 12 may be made of a metallic material that is non-corrosive, such as brass. The barbed fitting 12 may also include a flanged portion 17 which defines a stop for the barb clamp 10.

The barb clamp 10 includes a collet 18 and a sleeve 20. The collet 18 is an essentially annular member having a through aperture 19 for receiving the end of a tube 14 therein. The sleeve 20 is also an annular member with a through aperture 21 for receiving the end of the tube 14 as well as having a diameter for also receiving the collet 18 therein. The collet 18 and sleeve 20 should be made of an FDA approved material if the barb clamp 10 is in a medical or pharmaceutical environment. The material should be resilient. Preferably the collet 18 is made of acetyl, silicon, or polypropylene. The sleeve 20 is preferably made of polycarbonate, silicon, or polypropylene.

Figure 3:
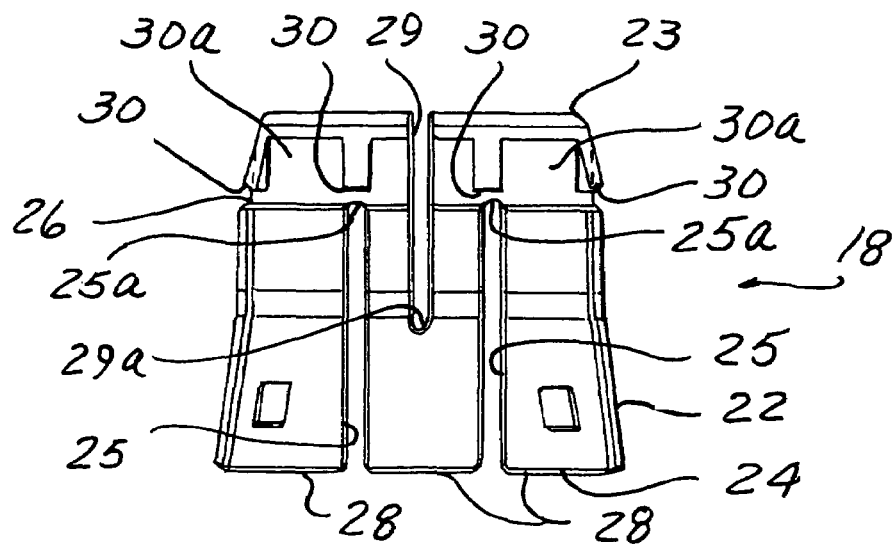
FIG. 3 is an elevational view of a collet in FIG. 1.
Figure 4:
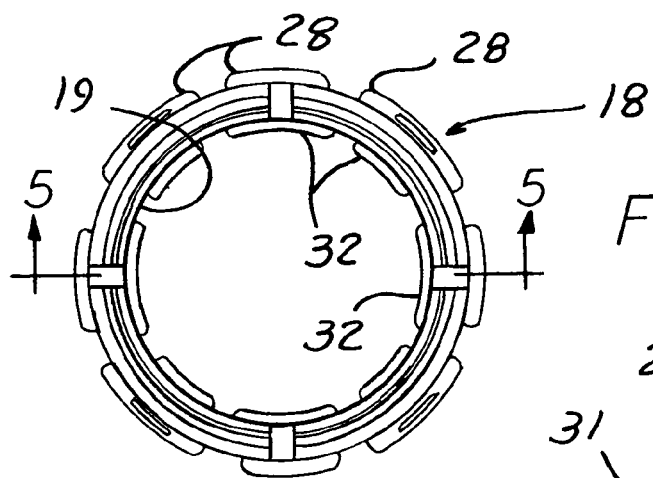
FIG. 4 is an end view of the collet in FIG. 1.
Figure 5:
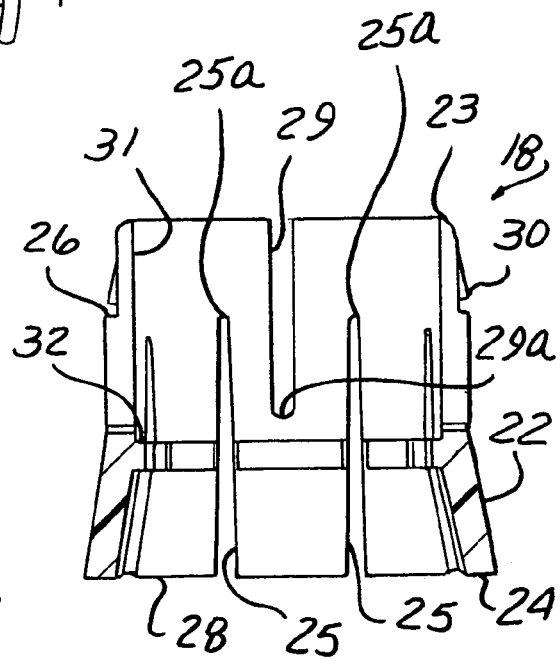
FIG. 5 is a sectional view of the collet taken along lines 5-5 of FIG. 4.
Figure 9:
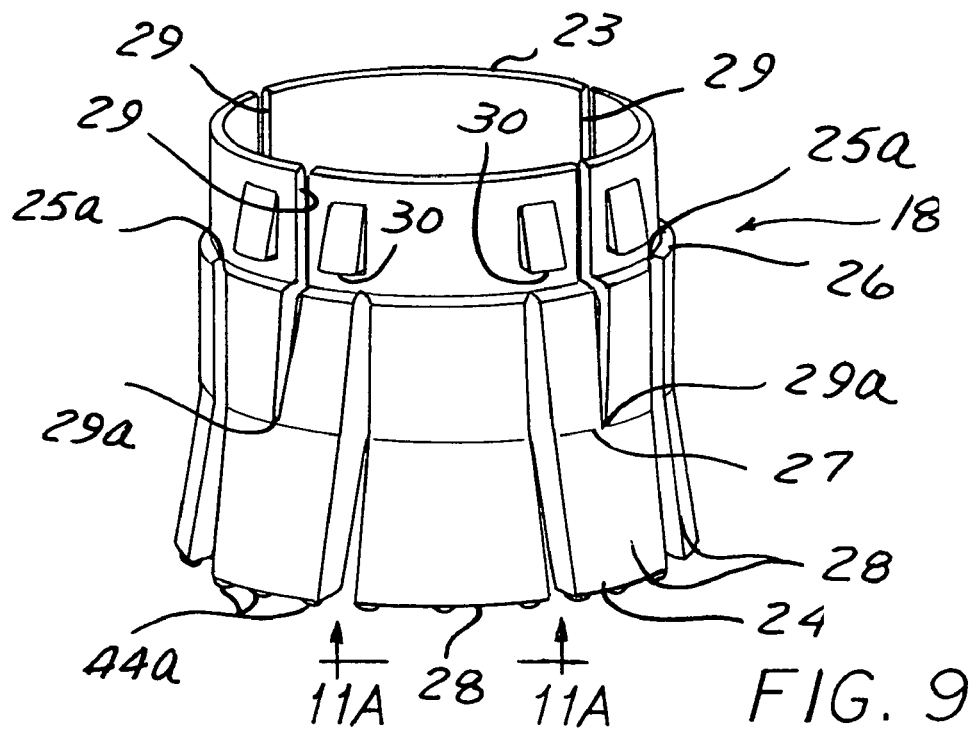
FIG. 9 is a perspective view of a second embodiment of the collet.
Figure 14:
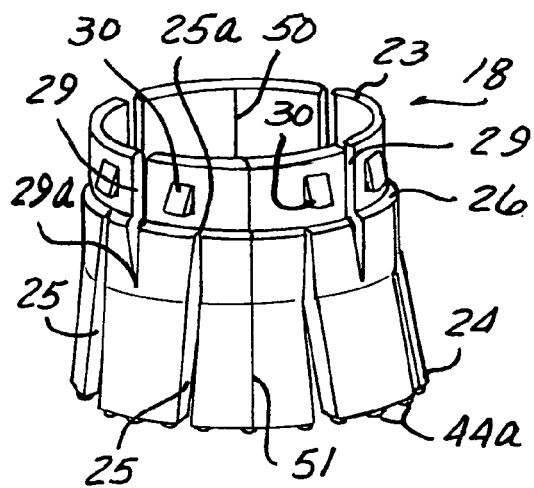
FIG. 14 is a perspective view of the collet shown in FIGS. 12 and 13.

Looking at FIGS. 3-5 the collet 18 has an exterior surface 22 providing resilient means for radially contracting around the tube 14. The collet 18 has a first end 23 forming a discontinuous annular ring. Along the exterior surface 22 and adjacent to the first end 23 is an annular groove 26. Moving toward the second end 24 and beyond the annular groove 26, the collet forms eight resilient tangs 28. The tangs 28 radially flare out or expand slightly at the second end 24 of the collet 18. The tangs 28 begin to flare approximately at the mid section 27 of each tang 28. The tangs 28 are formed by narrow through slots 25 extending from the second end 24 and terminating at the annular groove 26. The slots 25 are shown in FIGS. 3 and 5 with rounded termination ends 25a, however, the termination ends 25a may have pointed ends, as shown in FIGS. 9 and 14.

A small ramping ledge 30 projects above each termination end 25a of the narrow through slots 25. The small ledges 30 provide added strength to the collet and also provide a stop means for the sleeve 20, as will be discussed hereinafter. Between each small ledge 30 there is a recessed planar portion 30a extending into the annular groove 26. The eight tangs 28 form a resilient seal which allow the tangs to contract around a tubular member 14. Between every other tang 28 there is a through slot 29 which extends from the first end 23 to the mid-section 27 of the associated tang 28. The through slots 29 may also have rounded termination ends 29a as shown in FIGS. 3 and 5 or pointed termination ends 29a, as shown in FIGS. 9 and 14. The through slots 29 provide resiliency to the first end 23 of the collet 18 without sacrificing durability. The interior surface 31 of the collet 18 is essentially smooth except for a shelf 32 equally positioned on each tang 28 at the mid-section 27 for reasons to be discussed further.

Figure 6:
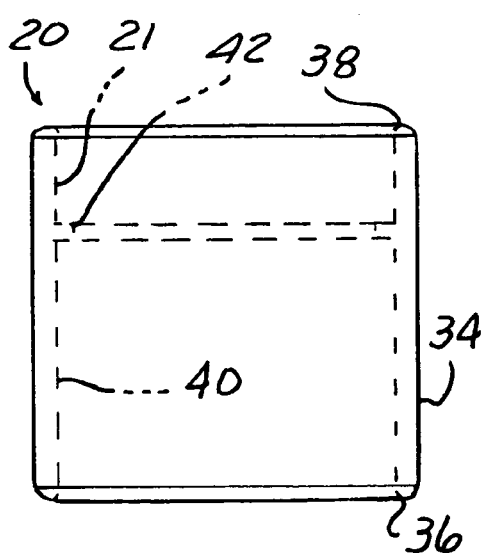
FIG. 6 is an elevational view of the sleeve in FIG. 1.
Figure 7:
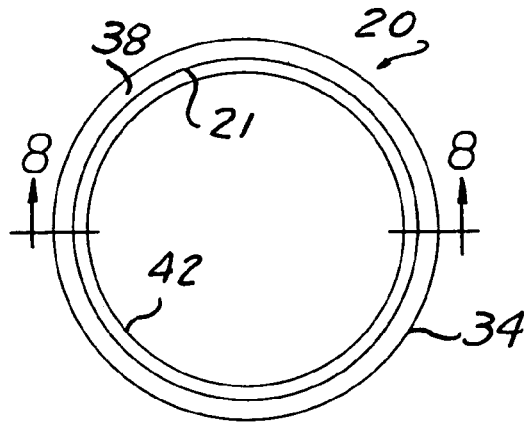
FIG. 7 is an top view of the sleeve in FIG. 1.
Figure 8:
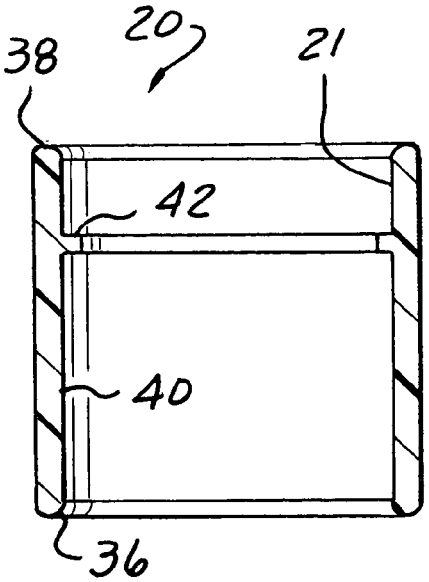
FIG. 8 is a sectional view of the sleeve taken along lines 8-8 of FIG. 7.

Looking at FIGS. 6-8, the sleeve 20 has a smooth exterior annular surface 34. The sleeve 20 has a first or bottom end 36 forming an arcuate base to facilitate assembly to the collet 18. The interior surface 40 forms a slight outward taper at the second or top end 38 of the sleeve 20. The interior surface 40 is essentially smooth throughout the length of the sleeve 20 except for an annular projection 42 that extends from the inner surface. The annular projection 42 is sized and positioned on the sleeve for disposition within the annular groove 26 of the collet 18 to form a lock when the barb clamp 10 is engaged. Therefore, the annular projection 42 is positioned proximate to the second or top end 38 of the sleeve 20.

The barb clamp 10 is connected with the barbed fitting 12 and tube 14 as discussed hereinafter and as shown in FIGS. 1 and 2. The sleeve 20 is first placed over the end of the tube 14 so that the second or top end 38 of the sleeve 20 is spaced furthest away from the tube end The collet 18 is then placed on the tube 14 so that the first end 23 of the collet 18 is closest to the sleeve 20. The expanded end 16 of the barbed fitting 12 is then placed into the tube 14. The expanded end 16 of the barbed fitting 12 is sized for being snugly received within the interior of the tube 14. The collet 18 is then slid over the tube 14 having the expanded end 16 of the barbed fitting 12 therein. The shelves 32 located on the interior surface 31 of the collet 18 is a retainer which forms a radial 360° compression around the tube 14 and under the expanded end 16 of the barb fitting 12 so that the barb fitting 12 cannot easily move out of the tube 14. The sleeve 20 is then slid over the collet 18 such that the first or bottom end 36 of the sleeve 20 initially encounters the first end 23 of the collet 18. As the sleeve 20 moves over the collet 18, the tangs 28 on the collet 18 are pushed radially inwardly into the tube 14 and barbed fitting 12, so that the annular shelf 32 of the collet 18 is pressed inwardly into the tube 14 and barbed fitting 12 to provide a tight seal therebetween and thereby lock the annular shelf 32 under the barb 16. The sleeve 20 continues over the collet 18 until the annular projection 42 on the interior surface 40 of the sleeve 20 sits within the annular groove 26 of the collet 18. The small ledges 30 on the exterior surface 34 of the collet 18 provides a stop and lock to prevent the annular projection 42 from moving out of annular groove 26. The barb clamp 10 "clicks" when the collet 18 and sleeve 20 lock together. The barb clamp 10 can then only be removed with the aid of a tool so that disconnection and leakages are prevented.

FIG. 9 shown an alternative embodiment of the collet 18. In this embodiment the through slots 25a are angularly configured to terminate with a pointed configuration. Likewise, the slots 29a that extend from the first end 23 to the mid-section 27 are angularly configured to terminate with a pointed configuration 35. The angular configuration of slots 25a and 29a allow the edges defining the slots to close and meet when the sleeve 20 is placed over the collet 18. When the sleeve 20 overlays the collet 18, the tangs 28 of the collet 18 are compressed so that the slots 25a are virtually closed without any gaps. Also, as the sleeve 20 is placed over the first end 23 of the collet 18, the first end 23 is compressed so that slots 29a are virtually closed without any gaps. The configuration of slots 25a and 29a allow the collet 18 to become essentially a continuous ring under the sleeve 20.

Figure 10:
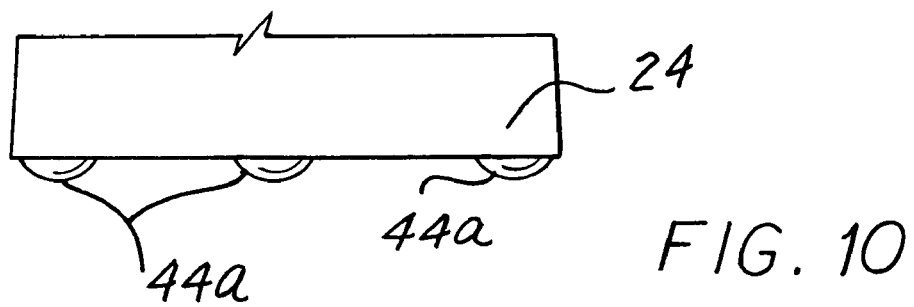
FIG. 10 is an partial end view of a tang on the collet of FIG. 9.
Figure 11A:
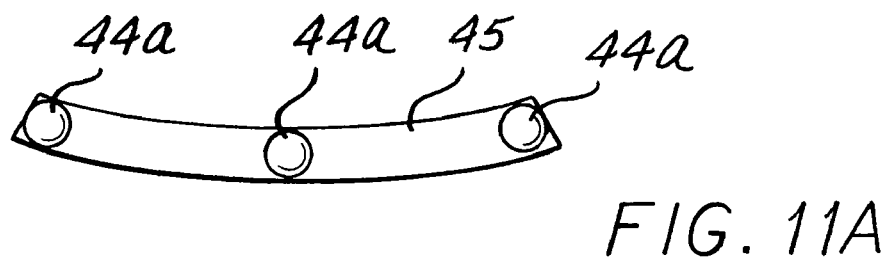
FIGS. 11a-b are partial edge views of a tang of the collet showing variations of a protuberance thereon.
Figure 11B:
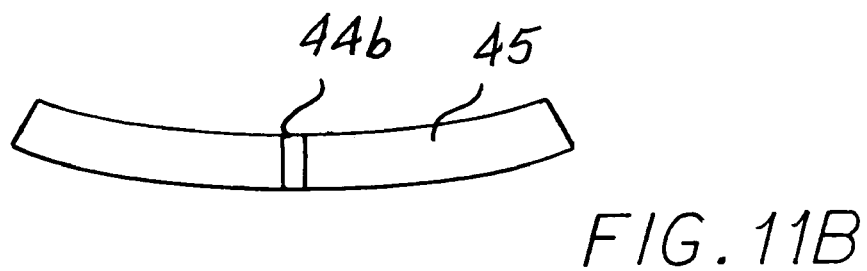

The alternate embodiment of the collet 18 as shown in FIGS. 9-11 also include protuberances in the shapes of spheres 44a, or elongate nodules 44b along the edge 45 of the second end 24. The protuberances 44a and 44b help to facilitate the full travel of the collet 18 during the assembly. There are preferably three protuberances 44a and 44b on each tang 28 as shown in FIGS. 9 and 11a. One protuberance 44a is adjacent the ends of each of the tang 28; and one protuberance 44a is in the center. However, as few as one protuberance 44a and 44b along the edge 45 of the tang 28 will facilitate the full travel of the collet 18 during assembly. The protuberances 44a and 44b have a diameter (for spheres 44a) or a length (for elongate nodules 44b) essentially equal to the depth of the tang 28.

Figure 13:
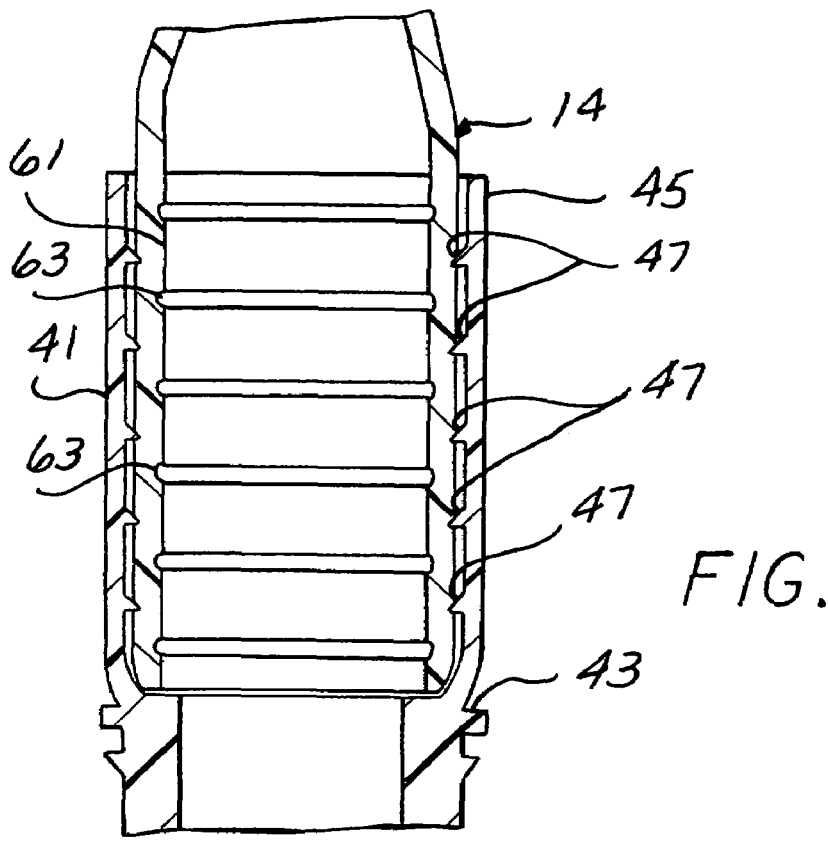
FIG. 13 is a sectional view of an interlock assembly.
Figure 12:
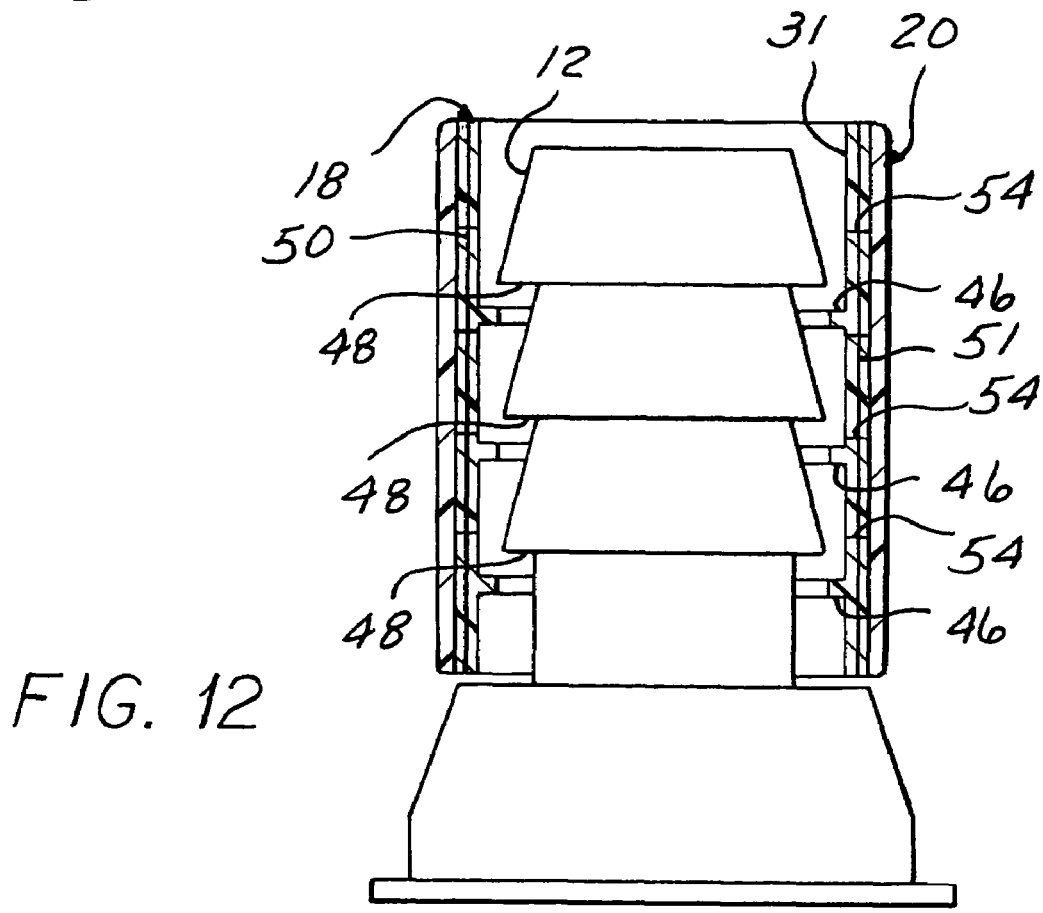
FIG. 12 is a sectional view of a barb clamp with a third embodiment of the collet.

In other embodiments of the collet 18, the collet 18 may include multiple retainers 46 to grip the barb fitting 12 and/or flexible tube 14. FIGS. 12 and 13 show a collet 18 with multiple retainers 46. Multiple retainers 46 are preferred when the barb fitting 12 has multiple barbs 48 extending therefrom to provide extra grip to the barb fitting 12. As can be seen in FIG. 12, two or more retainers 46 can extend from the interior surface 31 of the collet 18. The retainer 46 can be in the form of disconnected annular shelves 32 as disclosed in FIGS. 2 and 4 or as a continuous annular ring. The multiple retainers 46 are positioned along the interior surface 31 of the collet 18 to grip under multiple annular barbs 48. Although not required, preferably there is a retainer 46 for each annular barb 48 as shown in FIG. 12. The collet 18 shown on FIG. 12 may be formed by a conventional lost core molding process for the tubular configuration or by other conventional molding processes to provide a split seam 51 with interlocks 54 as discussed hereinafter, and especially with regard to FIGS. 14 and 15.

FIG. 13 shows another locking assembly wherein a fitting (not shown) from a source of fluid is attached to an interlock sleeve 41. The interlock sleeve 41 has a reduced first end 43 for connection to the fitting and an expanded second end 45 having internal radial locks 47. The interlock assembly also includes a tubular insert 61 having radial ribs 63 along the exterior surface of the insert 61. The interlock assembly is assembled by loading the tubular insert 61 into one end of a tubing 14. The tubular insert 61 is spaced from the end of the tubing 14 at a distance greater than the length of the expanded second end 45 of the interlock sleeve 41. The tubing 14 is inserted into the expanded second end 45 of the interlock sleeve 41 until the end of the tubing 14 meets the reduced portion 43 of the interlock sleeve 41. Contact with the reduced portion 43 of the interlock sleeve 41 forms a stop for the tubing 14. Once the tubing 14 is in place, the insert 61 is moved down into final assembly position where the insert 61 has one end 65 adjacent to the reduced portion 43 of the interlock sleeve 41. The reduced portion 43 of the interlock sleeve 41 has an inner diameter equal to the inner diameter of the tubing 14. The tubular insert 61 expands the tubing 14 into the internal radial locks 47 of the expanded end 45 of the interlock sleeve 41 so that the radial locks 47 grip the tubing 14. The radial ribs 63 on the exterior surface of the tubular insert 61 are positioned so that when the tubular insert 61 is fully inserted into the interlock sleeve 41, the radial ribs 63 on the tubular insert 61 are positioned between two adjacent radial locks in the interlock sleeve 41. This configuration provides a reliable and leakproof tubing connection.

Figure 15:
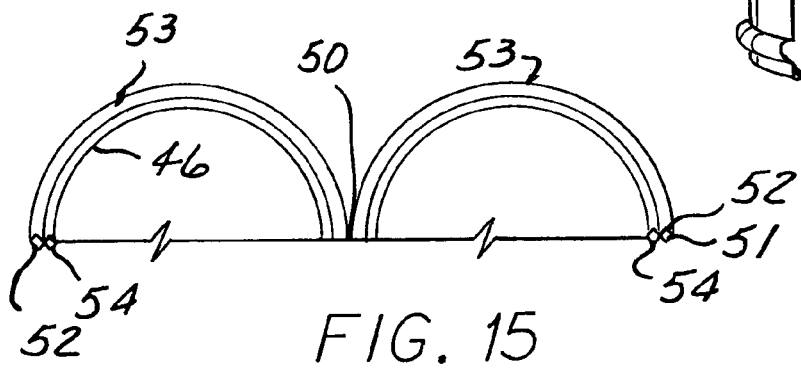
FIG. 15 is a top view of the collet shown in FIGS. 13 and 14 in an open position.

FIGS. 14 and 15 show that the collet 18 can be configured to open along one longitudinal side. The collet 18 can be provided with a living hinge 50 consisting of a thinning of the material along one longitudinal side. Opposite from the living hinge 50, the collet 18 can split along a seam 51 to form two clamshell halves 53 as shown in FIG. 15 that pivot about the living hinge 50. The two split ends 52 that form the seam 51 preferably have interlocks 54. One side of the interlock 54 is the female portion 54b and the other side is the male portion 54a. The interlocks 54 are preferably evenly spaced along the longitudinal length of the split 52. Preferably the female portions 54b and the male portions 54a switch sides of the seam 51 at each interval to prevent slippage between the two clamshell halves 53 after engagement. The clamshell halves 53 with the living hinge 50 of the collet 18 can be available on the collet 18 as shown in FIGS. 3, 5, 9, 12 and/or 13. However, the interlock features are most beneficial when the collet 18 is used on a barb fitting 12 with multiple barbs 48 to facilitate the installation of the collet 18 onto the tube 14 and barb fitting 12. The interlock 54 is shown and discussed in more detail with regard to FIGS. 23*b-d* and FIGS. 23*e-g*.

Figure 16:
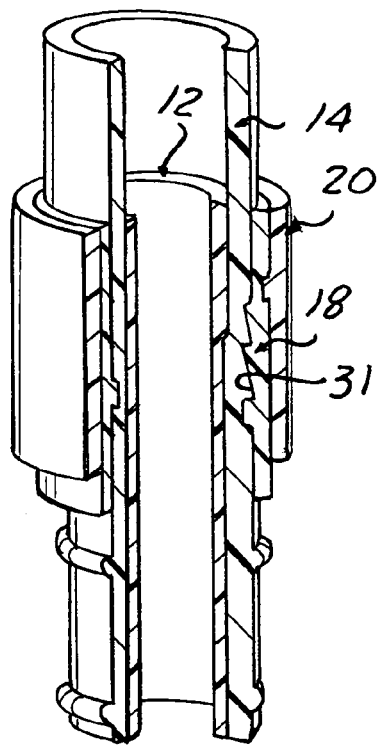
FIG. 16 is a perspective view with portions cut away of the barb clamp with a fourth embodiment of the collet.

FIG. 16 shows yet another embodiment of a collet 18. FIG. 16 shows that the collet 18 may have a unique shape along its inner surface 31 that forces the tube 14 to conform to the barb fitting 12. This unique shape of the collet 18 can be added to a single or multi-lock collet.

Figure 17:
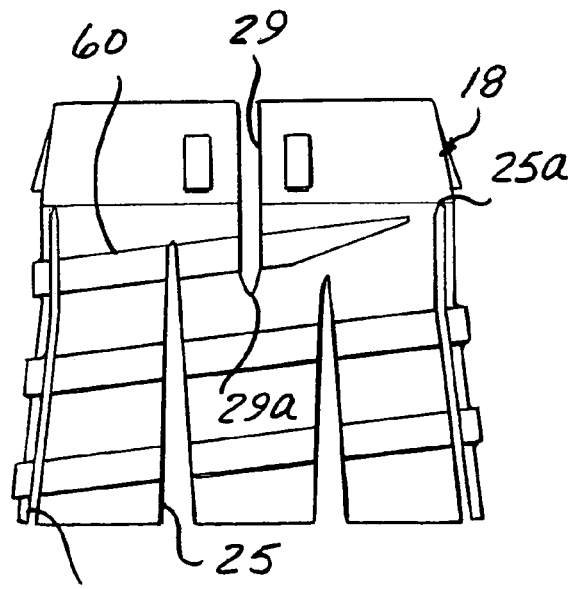
FIG. 17 is a side elevational view of a fifth embodiment of the collet.
Figure 18:
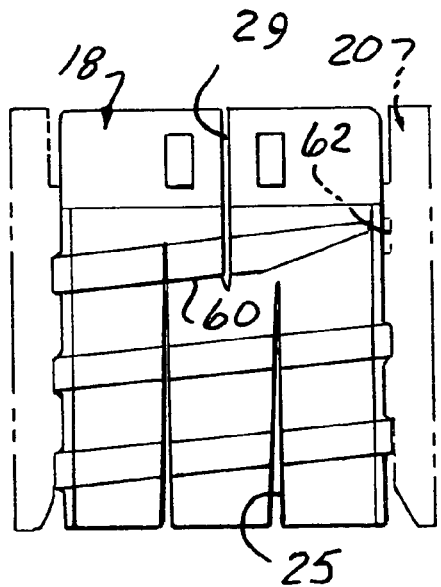
FIG. 18 is a side elevational view of the collet in FIG. 17 with the sleeve shown in phantom.

FIG. 17 shows a sixth embodiment of a collet 18. FIG. 17 is essentially the same collet 18 as shown in FIG. 9, but in addition includes an external thread 60 along most of the axial length of the exterior surface 22 of the collet 18. FIG. 17 shows the collet 18 in its unassembled open condition. FIG. 18 shows the collet 18 in FIG. 17 in its assembled condition disposed within a sleeve 20. A collet 18 with threads 60 as shown in FIGS. 17 and 18 can be inserted within a sleeve 20 either having a corresponding thread 62 on its inner surface 40 or having no corresponding thread on its inner surface 40.

FIG. 19 shows the collet 18 in FIG. 17 disposed within a sleeve 20 having a thread 62 molded on the inner surface 40 of the sleeve, which extends only a single time around the circumference of the inner surface 40 of the sleeve 20. FIG. 20 shows the collet 18 in FIG. 17 inserted within a sleeve 20 having a continuous thread 62 molded on and extending along the axially length of the inner surface 40 of the sleeve 20. The threaded surfaces on the collet 18 and sleeve 20 provide the advantage of ease of assembly of the sleeve 20 onto the collet 18 by a simple manual threading motion, either by hand or with an appropriate conventional tool. As the collet 18 is threaded into the sleeve 20, the ledges 30 on the exterior surface of the collet define a stop for the threading of the sleeve and also to hold the annular projection 42 of the sleeve 20 within the groove 26 of the collet 18 to provide a lock.

To further facilitate the threading of the sleeve 20 onto the collet 18, the exterior surface 34 of the sleeve 20 may include ribs 64 extending along the axial length of the surface 34. FIGS. 21 and 22 show the ribs that are located at 45° intervals from each other. The ribs 64 are essentially circular or bulbous in shape to provide concave surfaces 66 where the ribs 64 contact the exterior surface 34 of the sleeve. An appropriate tool such as a spanner tool 70 (FIGS. 45 and 46) can engage the ribs 64 by gripping into the concave surfaces 66 to facilitate the threading procedure. The ribs 64 may be provided on a sleeve 20 having either no interior thread 62, a single circumferential thread 62, or a full threaded inner surface 40.

Figure 24:
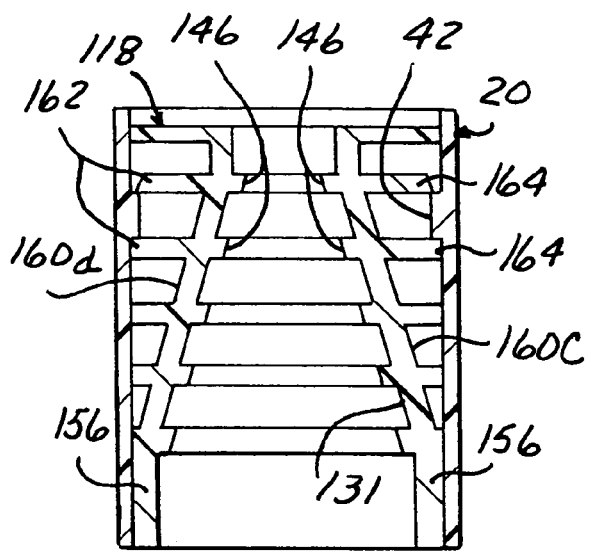
FIG. 24 is a sectional view of a sleeve mounted on the collet in FIG. 23a when the collet is in the closed position.

FIG. 23*a* shows yet another embodiment of the collet 118. FIG. 24 shows the collet 118 of FIG. 23*a* installed within a sleeve 20. Oftentimes, the medical and pharmaceutical industry uses filters having long tapered barbed ends connected between an external source of fluid and a patient. The long tapered barbed ends are a common connection point for the flexible tube 14 and therefore require a different configuration for the collet 18. A reliable leak-proof connection is provided with the collet 118 and sleeve 20 combination shown in FIG. 24 when installed over the long tapered barb fittings.

Looking at FIGS. 23*a* and 24, the collet 118 is shown with at least a portion of the exterior surface 122 and the interior surface 131 being tapered to correspond with a tapered barbed end of a filter (not shown). The collet 118 as shown in FIG. 23*a* is configured to open along one longitudinal side, similar to the collet shown in FIGS. 14 and 15. The collet 118 may be provided with a living hinge 150 consisting of a thinning of the material along the longitudinal side and preferably located at the centerline of the open collet 118. Opposite from the living hinge 150, the collet 18 can open or split along a seam to form two clam shell halves 153 as seen in FIG. 23*a*. The clam shell halves 153 are formed by exterior tapered walls 160*a,b,c,d*. The exterior tapered walls 160*a-d* forming the seams preferably have interlocks or wedges, 54*a* and 54*b* integrally formed thereon. The configuration of the collet 118 may also include a non-tapered wall portion 156 at each end of the tapered walls. The male portion 54*a* of the wedge is shown in FIG. 23*b* as a triangular extension. The female portion 54*b* of the wedge is shown in FIG. 23*c*, and has a complementary cavity 54*b* for receiving the male portion 54*a* of the wedge. FIG. 23*c* shows the male and female portions 54*a* and 54*b*, respectively, as connected into an interlock 54. The connection of the male and female portions 54*a* and 54*b*, respectively, of the wedge prevent lateral movement of the two clam shell portions 153 which form the collet 118. As can be seen in FIG. 23*a*, it is preferable to alternate the male and female portions 54*a* and 54*b*, respectively, of the wedges along the lateral side of the collet 18 to limit slippage between the two clam shell halves. When the two clam shell halves 153 are connected together, the wedge portions 54*a* and 54*b*, on the linear tapered column 160*a*, will connect to the male and female wedge portions 54*a* and 54*b*, respectively, in linear tapered column 160*d*. The male and female wedge portions on linear tapered column 160*b* will connect with the male and female wedge portions on linear tapered column 160*c*. The respective male and female interlock or wedge portions 54*a*, 54*b* on the associated non-tapered wall portions 156 will also lock.

The male and female interlocks may have other configurations such as shown in FIGS. 23*e-g*. The male portion 54*c* is shown in FIG. 23*e*. The female portion 54*d* is shown in FIG. 23*f* as a complementary cavity for receiving the male portion 54*c*. FIG. 23*g* shows the male and female portions 54*c* and 54*d* respectively as connected into an interlock 54. Other configurations, preferably angular, are acceptable for the interlocks.

Extending and connecting between walls 160*b* and 160*c* are internal ribs or tabs 164. Extending from walls 160*a* and 160*d* are external ribs or tabs 162. When the two clam shell halves 153 are connected together, the external ribs 162 that extend from tapered walls 160*a* and 160*d* meet and overlay each other to provide added strength to the collet 118. The internal tabs 164 that extend between tapered walls 160*b* and 160*c* will overlay each other when the two clam shell halves 153 are connected to also provide added strength to the collet 118. FIG. 24 shows the collet 118 in FIG. 23*a* within a sleeve 20 when the two clam shell halves 153 are connected together, the external tabs or ribs 162 extending from the tapered walls 160*a* and 160*d* of the collet have varying lengths so that they each terminate at the same plane. Further, the internal tabs or ribs 164 when overlaid also terminate along the same plane. The tabs or ribs 162 and 164 have a length such that they fit snugly within the sleeve 20. Therefore, the tabs or ribs 162, 164 have a dual function of providing extra strength to the collet 118 as well as providing a snug fit of the collet 118 within a sleeve 20. The annular projection 42 on the sleeve will be secured in place between adjacent tabs or ribs 162, 164 on the collet 118.

Further, as shown in FIG. 23*a* and especially FIG. 24, the tapered collet 118 may include multiple locks 146 extending from the interior surface 131 of the collet 18. The retainers 146 may be in the form of a discontinuous shelf or as a continuous annular ring. The multiple retainers 146 are preferred when the barb fitting has multiple barbs extending therefrom to form an extra grip to the barb fitting. Preferably, there is a retainer 146 for each annular barb on the tapered fitting.

Figure 25:
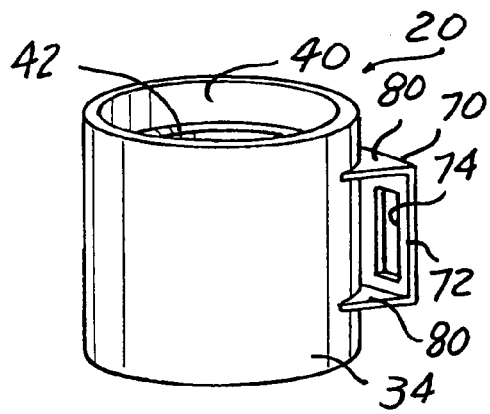
FIGS. 25-27 are perspective views of the sleeve having a mounting bracket with various configurations attached thereon.
Figure 26:
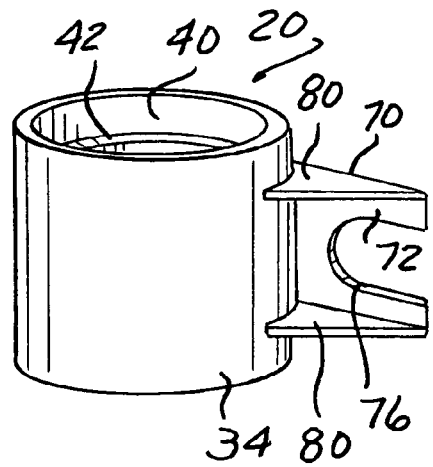
Figure 27:
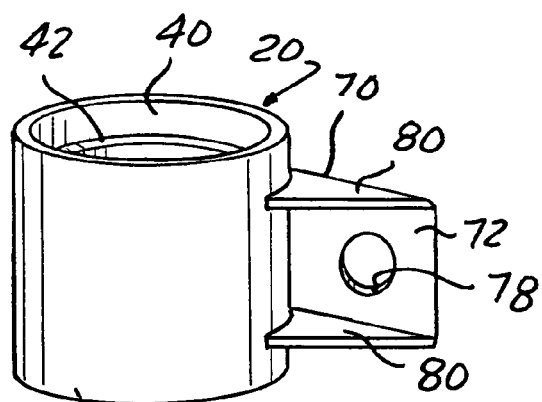

The sleeve 20 may also include varying configurations or features to accommodate the requirements of the user. The sleeve 20 may be configured to include one or more mounting brackets 70 attached to the exterior surface 34 of the sleeve 20. The sleeves 20 as shown in FIGS. 25-28 are essentially the same as the sleeve 20 shown in FIGS. 6-8. The sleeve in FIGS. 25-28 has a smooth exterior annular surface 34. Although not shown in FIGS. 25-28, the interior surface 40 is also essentially smooth throughout the length except for an annular projection 42 that extends from the inner surface. As stated, supra, the annular projection 42 is sized and positioned on the sleeve 20 for disposition within the annular groove 26 of the collet 18 when the connector 10 is engaged or between adjacent tabs or ribs 162, 164 of the collet 118. The bracket 70 on the exterior surface 34 of the sleeve 20 includes a planar member 72 extending from the exterior surface 34 of the sleeve. The planar member 72 can include a narrow slit 74 formed therethrough (FIG. 25), a slot 76 formed therethrough (FIG. 26), or a hole 78 formed therethrough (FIG. 27). The planar member 72 having the slit 74, slot 76, or hole 78 may be supported on the exterior surface 34 of the sleeve 20 by a pair of flanges 80. Each flange 80 is positioned on opposing sides of the planar member 72 and connected to the exterior surface 34 of the sleeve 20. Although, the slit 74, slot 76, and hole 78 shown in FIGS. 25-27 show typical aperture configurations to allow connection to typical known external device, the aperture configuration shown in the mounting brackets 70 in FIGS. 25-27 may vary according to the particular requirement.

Figure 28:
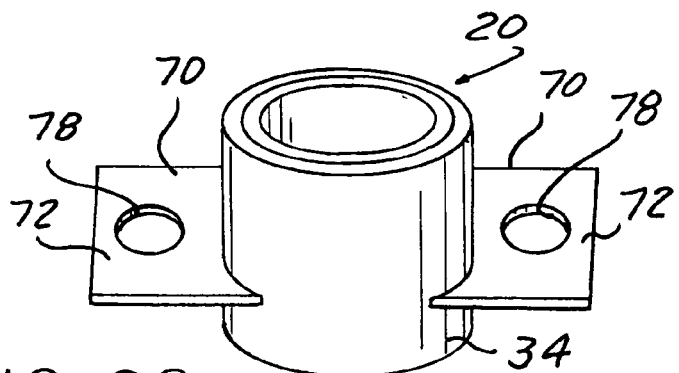
FIG. 28 is a perspective view of the sleeve having multiple mounting brackets attached thereon.

In addition, multiple external devices may be required for connection to the barb clamp via the sleeve. Therefore, FIG. 28 shows multiple brackets 70 connected to the sleeve 20. FIG. 28 also shows that the bracket 70 may be orientated onto the exterior surface 34 of the sleeve 20 in vertical, horizontal or various angled orientations thereto. Further, FIG. 28 shows that the planar member 72 of the bracket 70 may not necessarily be supported by brackets 80. The mounting brackets 70 as shown in FIGS. 25-28 are preferably integrally molded to the sleeve 20.

Figure 29A:
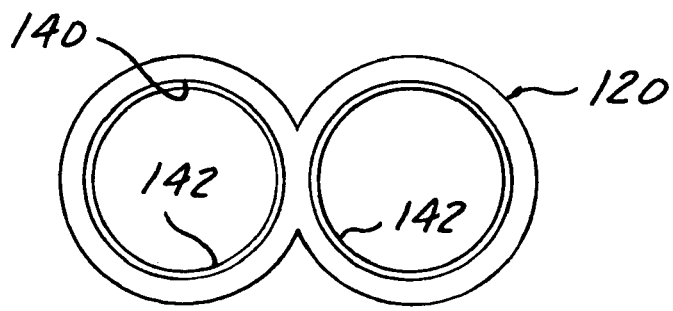
FIG. 29a is a top view of a pair of sleeves connected together.
Figure 29B:
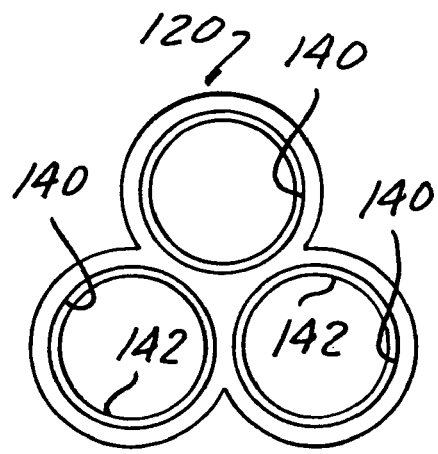
FIG. 29b is a top view of three sleeves connected together.
Figure 29C:
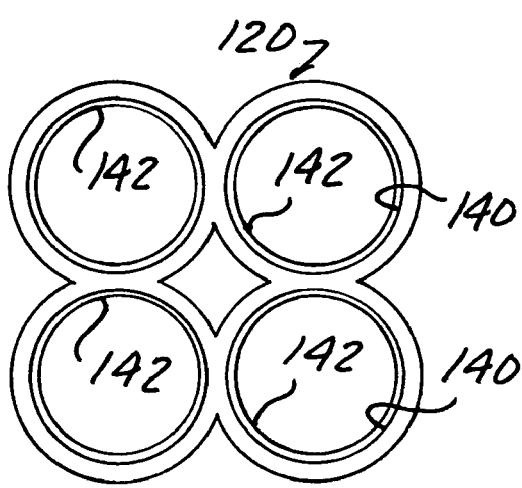
FIG. 29c is a top view of four sleeves connected together.

Some applications may require multiple or manifold arrangements so that multiple flexible tubing can be connected to multiple sources of fluid. It may further be necessary to maintain these flexible tubings in close proximity to each other. Therefore, the barbed clamp 10 also features multiple sleeves 20 integrally molded as a single component. FIGS. 29a-29c show three variations of the multiple sleeves 120. The interior surfaces 140 will be the same as the interior surface 40 of the sleeve 120 shown in FIGS. 6-8. Each of the connected sleeves 120 will include an annular projection 142 that extends from the interior surface 140. The annular projection 142 is sized and positioned in each sleeve 120 to be positioned within the annular groove 26 of an individual collet 18 or to be positioned between adjacent tabs or ribs 162, 164 on the collet 118 when the barb clamp 10 is engaged. The numbers of multiple sleeve 120 manifolds are not located by the manifolds shown in FIGS. 29a-c.

Figure 30A:
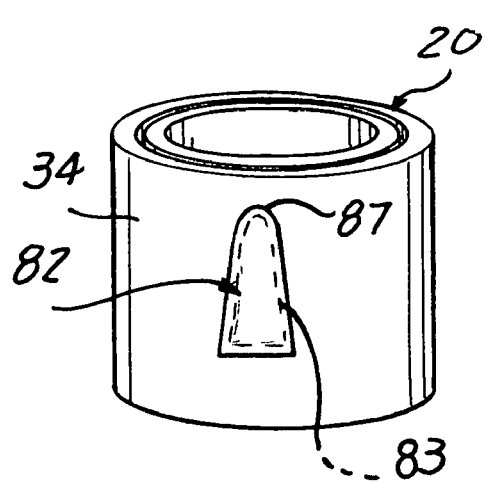
FIGS. 30a-b are perspective views showing sleeves having attachment components.
Figure 30B:
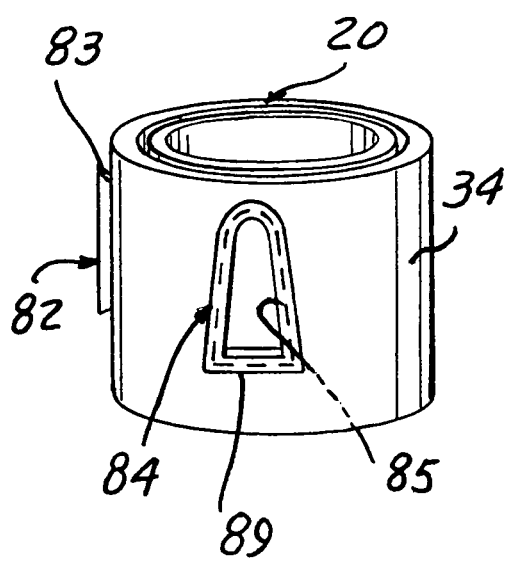
Figure 30C:
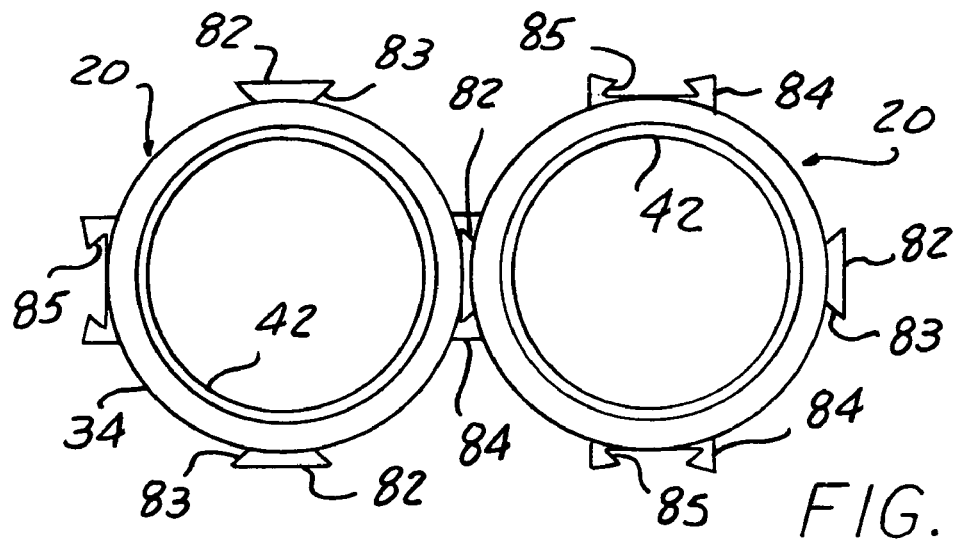
FIG. 30c is a top view showing multiple sleeves connected to each other by means of the attachment components shown in FIGS. 30a-b.
Figure 31:
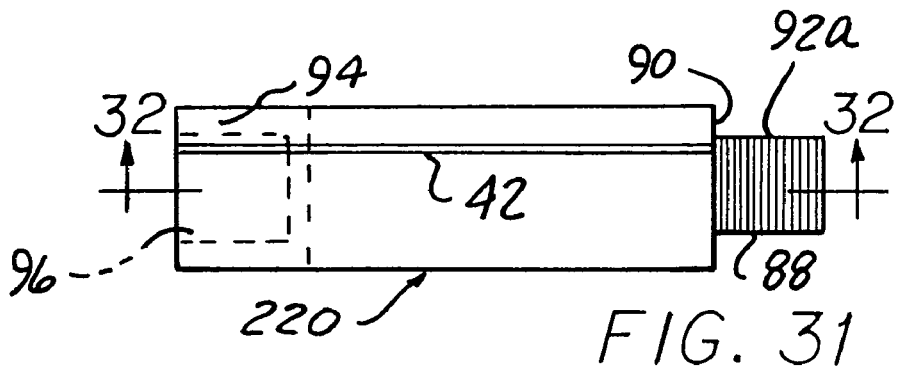
FIG. 31 is another embodiment of a sleeve formed in a flat formation.

FIGS. 30a and 30b show an alternative configuration and means for connecting individual sleeves 20 together. One means to connect adjacent sleeves 20 is to include attachment means to the exterior surface 34 of the sleeve such as shown in FIGS. 30a and 30b. The attachment means includes a male attachment extension 82 and a female attachment cavity 84. In the embodiments shown in FIGS. 30a and 30b, male attachment extension 82 and its corresponding female attachment cavity 84 have a dove tailed configuration that are molded directly onto the surface of the sleeve 20. The dove tail extension 82 has an outwardly tapered wall 83. The attachment cavity 84 form a slot 85 configured for receiving the dove tail extension 82. The male attachment extension 82 can be inserted into the female attachment cavity 84 by sliding the top end 87 of the male attachment extension 84 into the bottom end 89 of the female attachment cavity 84. Once the male attachment extension 82 is fully within the female attachment cavity 84, the corresponding sleeves 20 can not be laterally pulled apart. Although only one male attachment extension 82 and one female attachment cavity 84 is shown in the drawings, it is possible that as many as eight attachment components could be placed on a single sleeve 20. Preferably, the eight attachment components 82, 84 would alternate between male to female attachment components around the exterior circumference of the sleeve 20. FIG. 30c shows a top planar view of a pair of sleeves 20 connected to each other by means of the male and female attachment components 82, 84.

FIGS. 31-33a, *b* show another embodiment of a sleeve 220 which is molded in a flat formation and which can be wound around a collet 18 and locked in place. A projection 42a is positioned proximate to the second or top end 38a of the sleeve 220. The projection 42a is sized and positioned on the sleeve 220 for disposition within the annular groove 26 of a collet 18, as shown in FIGS. 3-5. As further shown on FIGS. 31-32, a tab 88 extends from a first end 90 of the sleeve 220. Teeth 92a traverse the width of the tab 88. On the second end 94 of the sleeve 220 a pocket formation 96 is formed. On the upper interior surface 98 of the pocket 96 are complimentary teeth 92b traversing the width of the pocket 96. This embodiment of the sleeve 220 is wound directly over a collet 18 already positioned over a barb fitting end tube 12 and 14. The sleeve 220 is sized so that when wound over the collet 18, the tab 88 can be inserted within the pocket 96.

Figure 33A:
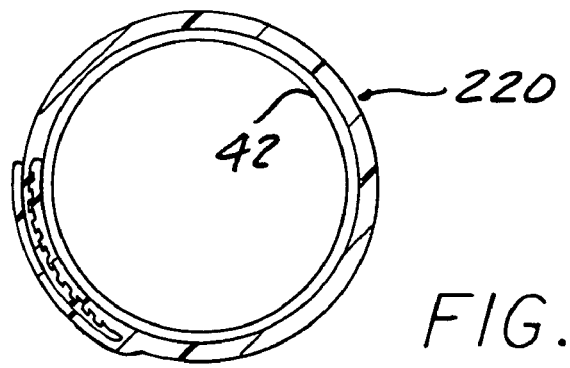
FIG. 33a shows a top view of a portion of the sleeve in FIG. 31 in a locked formation.
Figure 33B:
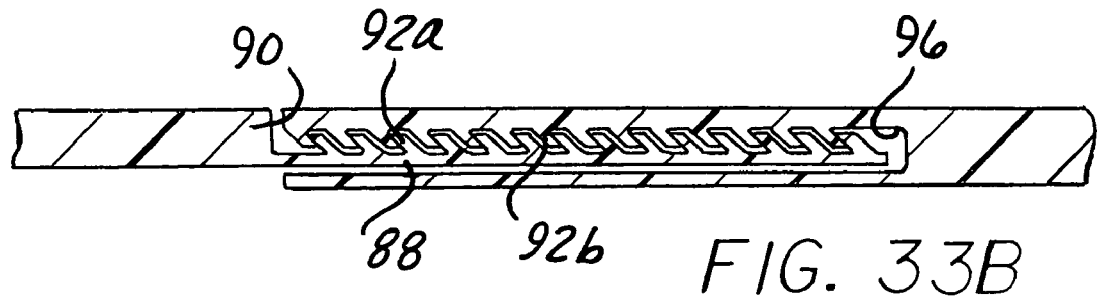
FIG. 33b is a sectional view of an enlarged portion of the sleeve in FIG. 31 in a locked formation.

FIG. 33a shows the respective ends of the sleeve 220 connected. As can be seen in FIG. 33b the teeth 92a, 92b on the respective ends of the sleeve 220 are angled to allow for the tab 88 to be easily inserted within the pocket 96. However, once the teeth 92a and 92b are locked in place, the angular formation of the teeth 92a, 92b on the tab 88 and in the pocket 96 resist movement of the first end 90 of the sleeve 220 out of the pocket 96.

Figure 32:
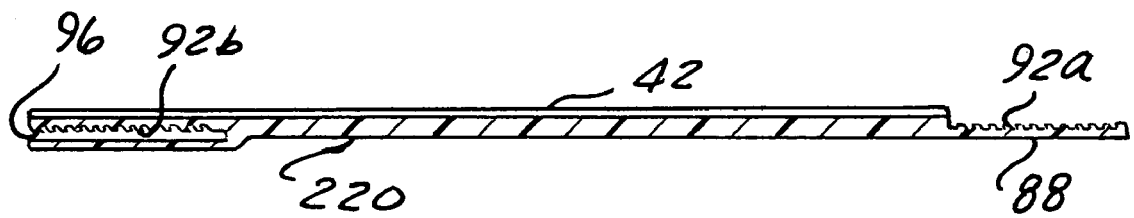
FIG. 32 shows a cross-sectional view of the sleeve shown in FIG. 31 along lines 32-32.
Figure 34:
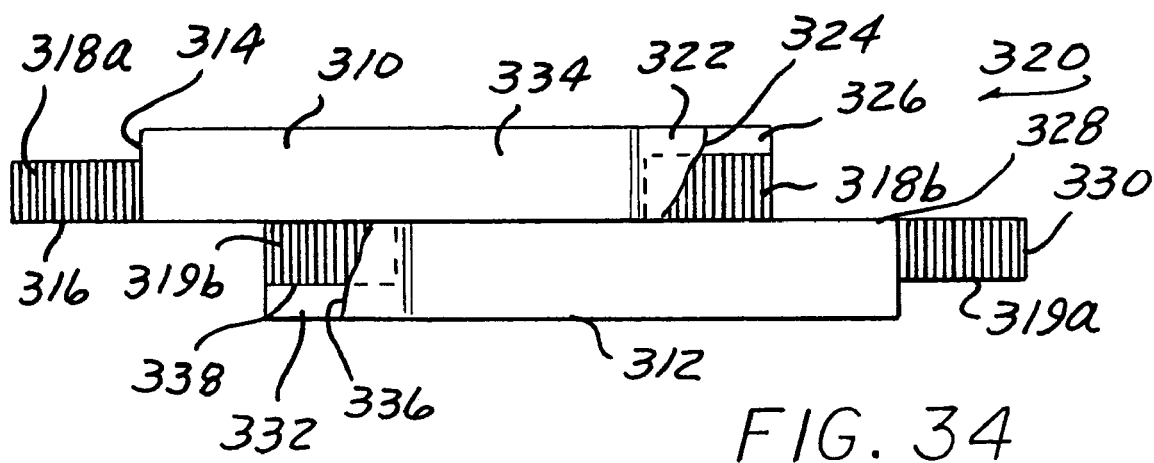
FIG. 34 is a side elevational view of an outer surface combination sleeve and collet formed in a flat formation.

FIG. 34 shows another embodiment of the sleeve 320 molded in an essentially flat, planar formation which further includes a collet integrally molded therein. FIG. 34 shows the outer surface 334 of the combination sleeve and collet 320. For reasons detailed hereinafter the combination sleeve and collet 320 is molded in a flat formation having an upper portion 310 and a lower portion 312 offset from each other. The upper portion 310 has a first end 314 having a tab 316 extending therefrom, the tab 316 has teeth 318a traversing the width of the tab 316. The upper portion 310 has a second end 322 forming a pocket 324 similar to that shown in FIG. 32. The pocket 324 also has complementary teeth 318b on an interior surface 326 of the pocket 324. The lower portion 312 is integrally molded to the upper portion 310 and offset therefrom. The lower portion 312 has a first end 328 with a tab 330 extending therefrom. The tab 330 of the lower portion 312 is at the opposing end as the tab 316 in the upper portion 310. The tab 330 has teeth 319a traversing the width of the tab 330. The lower portion 312 has a second end 332 having a pocket 336 similar to that as shown in FIG. 32. The pocket 336 also has complementary teeth 319b on an interior surface 338 of the pocket 336. Sleeve 320 works well with a collet 18 when disassembly of the tube and fitting is not possible.

Figure 35:
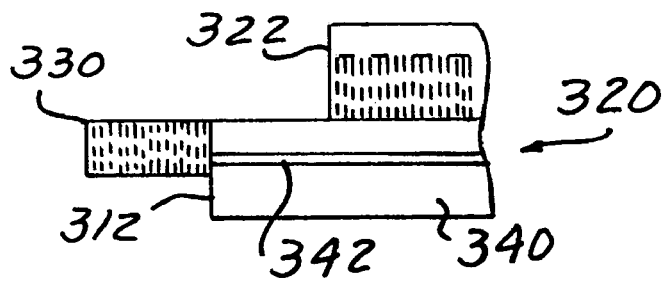
FIG. 35 is a portion of a side elevational view of an inner surface of the combination sleeve and collet.

FIG. 35 shows a portion of the inner surface 340 of the combination sleeve and collet 320. The inner surface 340 includes a shelf or projection 342 for gripping into a barb end 16. The projection 342 is located on the inner surface 340 of the lower portion 312 to correspond to the barb end 16. Because the combination sleeve and collet 320 is wound around a barb 12 in a sealing formation, the offset of the upper and lower portions 310, 312 of the combination sleeve and collet 312 overlaps any gap that would be formed by the winding process around the varying circumference of a barb fitting 12.

Figure 36:
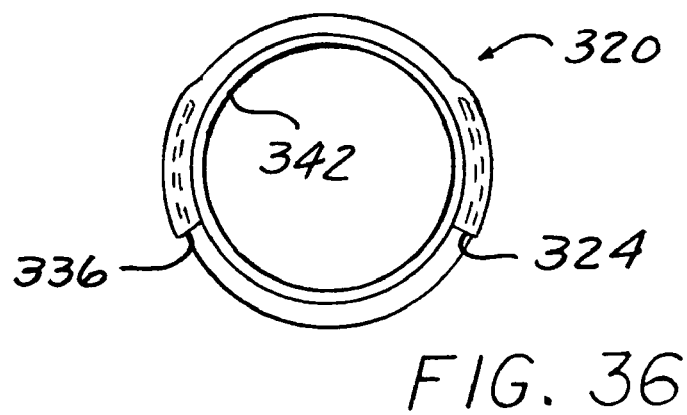
FIG. 36 is a top view of the combination sleeve and collet in a locked formation.

To lock the combination sleeve and collet 320, the tab 316 of the upper portion 310 is inserted into the pocket 324 of the upper portion 310; and the tab 330 of the lower portion 312 is inserted into the pocket 336 of the lower portion 310. The teeth 318a, 319a on both tabs 316, 330 and the teeth 318b, 319b in the pockets 324, 336 function in the same manner as discussed supra regarding FIG. 33b. FIG. 36 shows the combination sleeve and collet 320 in a locked position.

Figure 37:
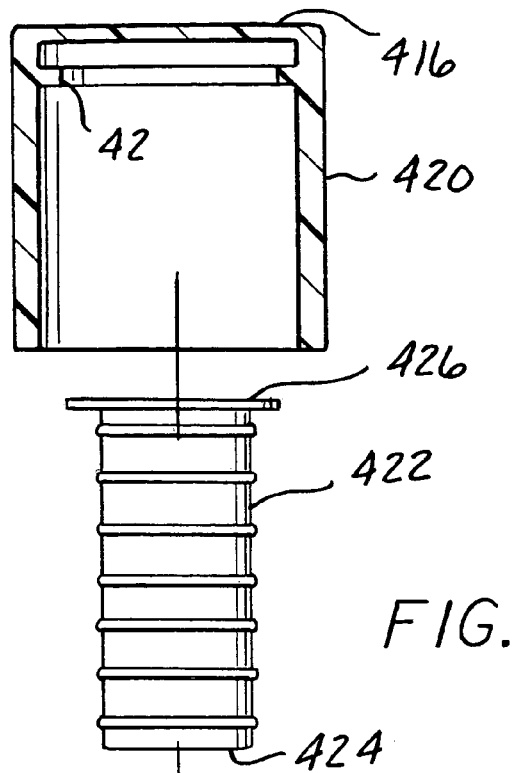
FIG. 37 is an exploded view of a cap lock assembly.

There will be instances in which one may want to cap off the tubing 14 leading from a sterile system. In these instances a sleeve 420 having a capped end 416, preferably together with an interlocking plug 422 can be used to form a caplock assembly 410. FIG. 37 shows an exploded view of a sleeve 420 having an end cap 416 integrally molded thereon, an interlocking plug 422, and a collet 18. The sleeve 420 will essentially have the same characteristics as the sleeve shown in FIGS. 6-8 but will further include a capped end 416 to form a closure. An interlocking plug 422 will replace a barb fitting 12. The interlocking plug 422 has a cylindrical formation with at least one open end 424 and preferably one closed end 426. The closed end 426 will further ensure that there is no leakage. The collet 18 is the same collet as shown in FIGS. 3-5, however, any of the other previously disclosed collets may be used.

Figure 38:
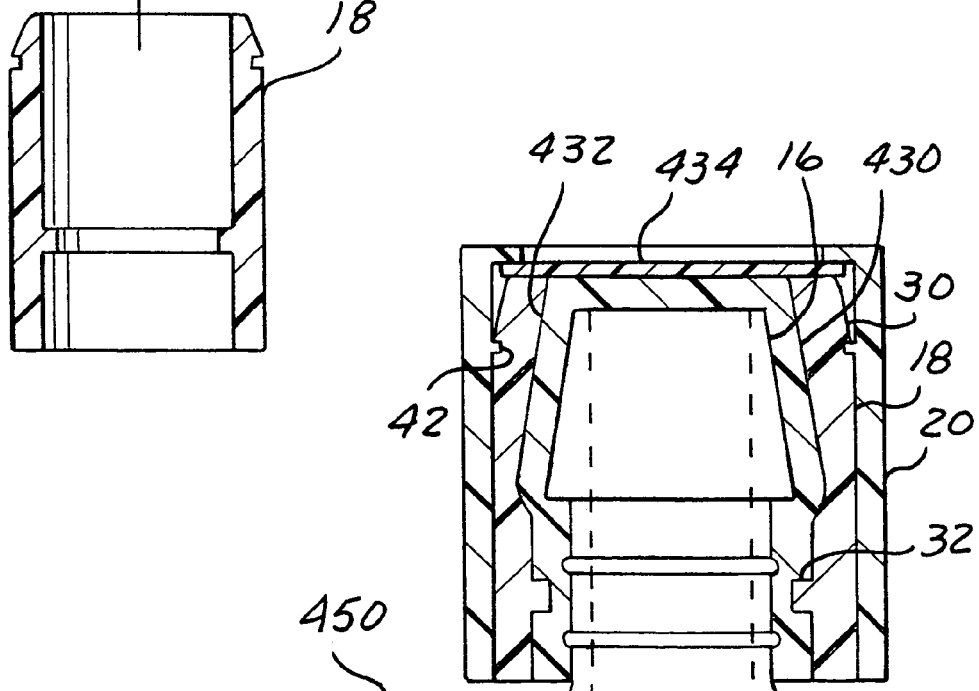
FIG. 38 is a sectional view of another embodiment of the cap lock assembly.

Another embodiment of a caplock assembly (FIG. 38) is available primarily for means to ship a product of fluid in a container 450 having a barb fitting access port. The caplock assembly includes a collet 18 and sleeve 20, as discussed supra, and a tubular seal 430 with one end closed 432 and a disc-shaped top 434. The tubular seal 430 is placed over the barb fitting 16 so that the closed end 432 is over the exposed end of the barb fitting 16. A collet 18 is then positioned over both the tubular seal 430 and barb fitting 16. The disc-shaped top 434 is then placed on the closed end 432 of the tubular seal 430 before the sleeve 20 is installed over the collet 18. The relationship of the sleeve 20 and collet 18, when assembled on the tubular seal 430, is the same as discussed relative to FIG. 1. The caplock assembly provides a superior seal during the transport or storage of a filled container 450.

To provide ideal engagement between the barb clamp and a barb fitting 12 and tube 14 it is important that the retaining ring inner or shelves 32 diameter on the collet 18 is less than the barb fitting outer diameter. Testing has shown an increase of 30% when this ideal engagement is achieved. Depending upon the customer application and pull off requirement, the smaller the retaining ring inner diameter the better the sealing and integrity of the barb clamp of the present invention.

Figure 39:
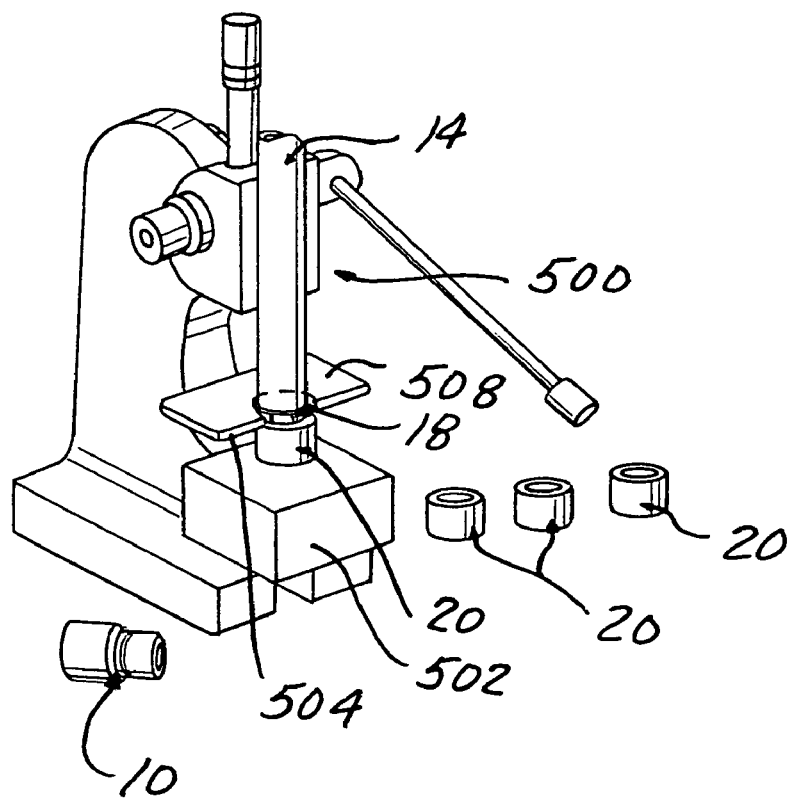
FIG. 39 is a perspective view of tool for assembling the barb clamp.
Figure 40:
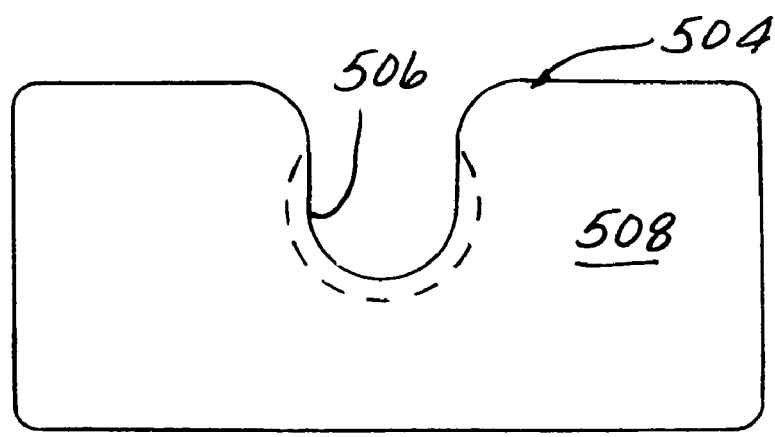
FIG. 40 shows the plate for the tool in FIG. 39.

To facilitate the assembly of the barb clamp 10, tools have been provided or retrofitted for the assembly process. FIGS. 39 and 40 show one type of tool used to assemble the barb clamp 10 together. A tube 14 having a barb fitting at one end is held in a vice 500. A collet 18 is threaded through the tube 14 and placed adjacent the barbed end over a stop block 502. The vice tool 500 is fitted with a movable plate 504. The moveable plate 504 is placed adjacent to the collet 18 so that the collet 18 is sandwiched between the movable plate 504 and block 502. The movable plate 504 has an arcuate slot 506 cut into one side. The arcuate slot 506 is sized to allow the tube 14 through the slot 506, but to prevent the collet 18 from passing through. By placement of the assembler's hands on the planar surface 508 adjacent each side of slot 506, the downward movement of the plate 504 toward the block 502 will force the collet 18 onto the barbed fitting and tube. The plate is preferably made of stainless steel. The plate 504 in FIG. 40 is shown in more detail in FIG. 24. The same procedure is used to lock the sleeve 20 onto the collet 18. When the sleeve 20 is to be installed onto the collet 18, a movable plate 504 having an arcuate slot 506 to allow the collet 18 through the slot 506, but prevents the sleeve 20 from passing therethrough.

Figure 41:
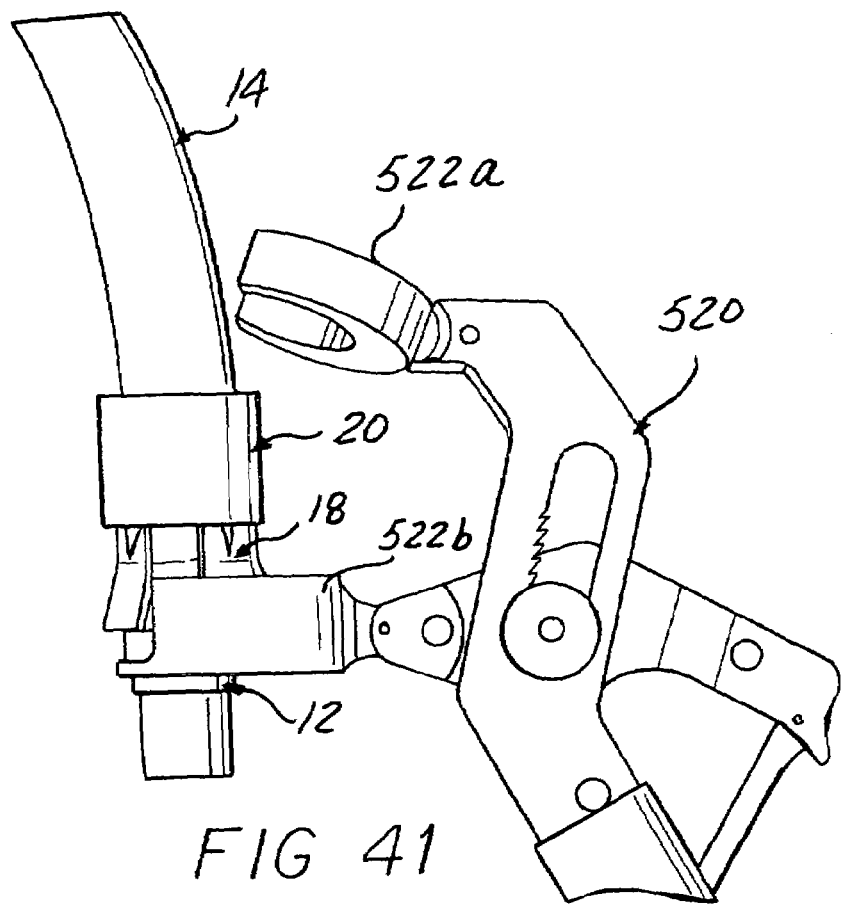
FIG. 41 is a perspective view of a hand tool for assembling the barb clamp.
Figure 42A:
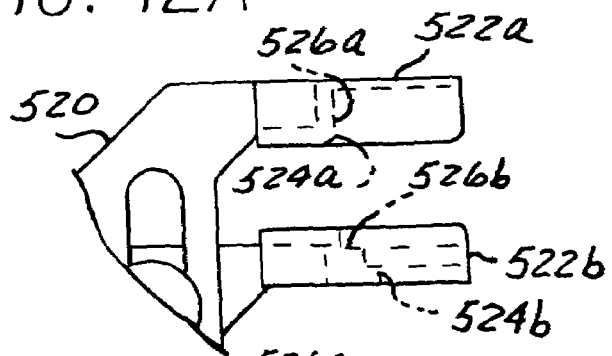
FIGS. 42a-d show a first configuration of the jaws in FIG. 41 in a closed position, open position, bottom view of the upper jaw, and top view of the lower jaw, respectively.
Figure 42C:
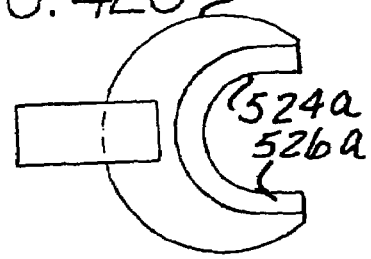
Figure 42B:
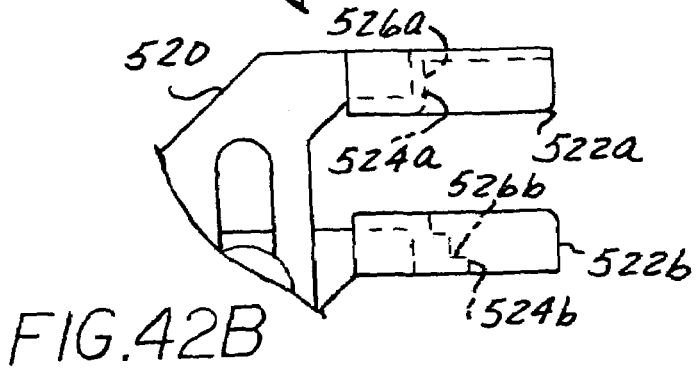
Figure 42D:
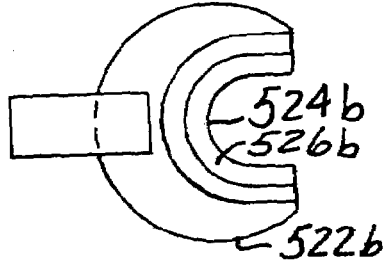

FIG. 41 shows a hand tool 520 for assembling the barb clamp 10. The hand tool is a standard tool such as a Robo Grip® tool 520 that is fitted with upper and lower end jaws 522a, 522b configured to hold and clamp the collet 18 and sleeve 20 over the barb fitting 12 and tube 14. To prevent rust formation, the upper and lower end jaws 522a, 522b are made of stainless steel material. Because the barb clamp 10 can be different sizes and configurations, the upper and lower jaws 522a, 522b must have various accommodating configurations. FIGS. 42a-d to 44a-d show details of various configurations envisioned. The lower jaw 522b, as shown in FIGS. 42a,b,d, 43a,b,d, and 44a,b,d, is configured to hold the tube 14 with the barb fitting therein. The collet 18 in position over the tube 14 within an arcuate slot 524b having at least one step 526b forming the slot in the lower jaw 522a. Looking at FIGS. 42d, 43d, and 44d, it is evident that various sized arcuate slots having different step dimensions are available to accommodate the various sized barb clamp components.

The upper end jaw 522a will generally have an arcuate slot 524a that is larger than the lower end jaw slot 524b to grip around the sleeve 20. Although it is preferred that the upper end jaw 522a has a larger arcuate slot 524a than the lower end jaw 522b, there will be instances when it may be desirable that the upper end jaw 522a has a smaller arcuate slot 524a than the lower end jaw 522b. Such a configuration is shown in FIGS. 44c and 44d. The upper jaw 522a is formed by at least one step 526a. During installation, as the lower end jaw 522b is gripping the collet and tube end, the upper end jaw 522a grips the sleeve 20, while the upper and lower end jaws 522a and 522b, respectively, are in the open position. As the hand tool 520 is closed or is moved to the closed position, the upper and lower end jaws 522a, 522b, respectively, move toward each other. As the upper end jaw 522a, having the sleeve 20 within its arcuate slot 524a, moves closer to the lower end jaw 522b, the sleeve 20 is slid into position over the collet 18 by the upper end jaw 522a, The sleeve 20 is in place when the annular projection 46 slides and "clicks" into the annular groove 26 of the collet 18.

Figure 45:
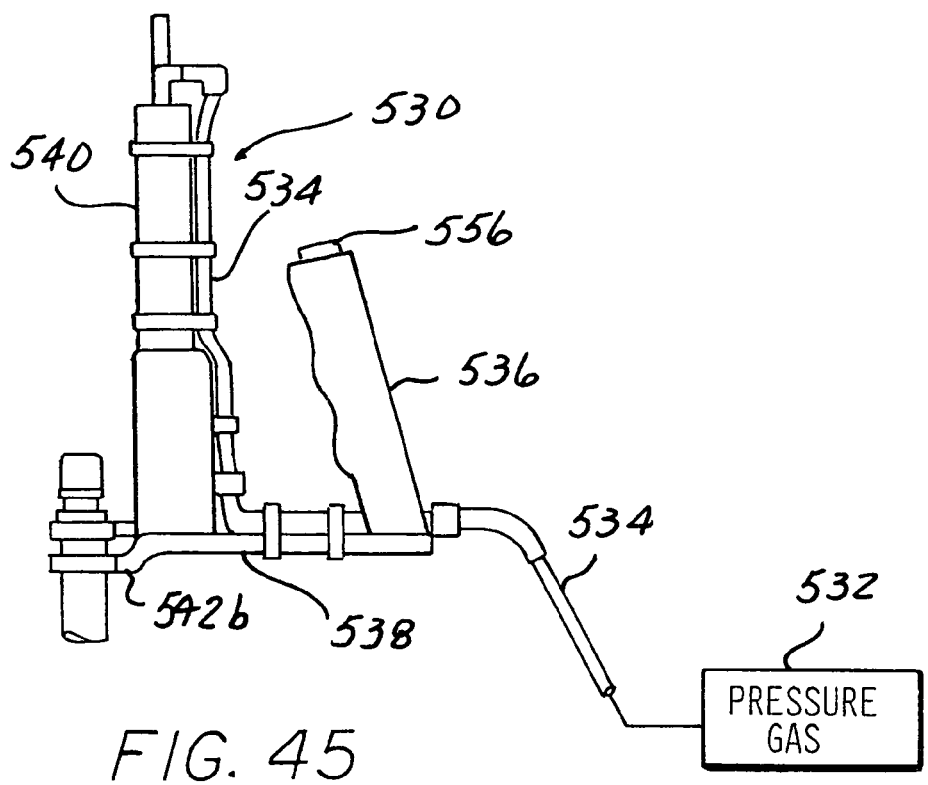
FIG. 45 is a side elevational view of a pneumatically operated tool to assemble the barb lock.
Figure 46:
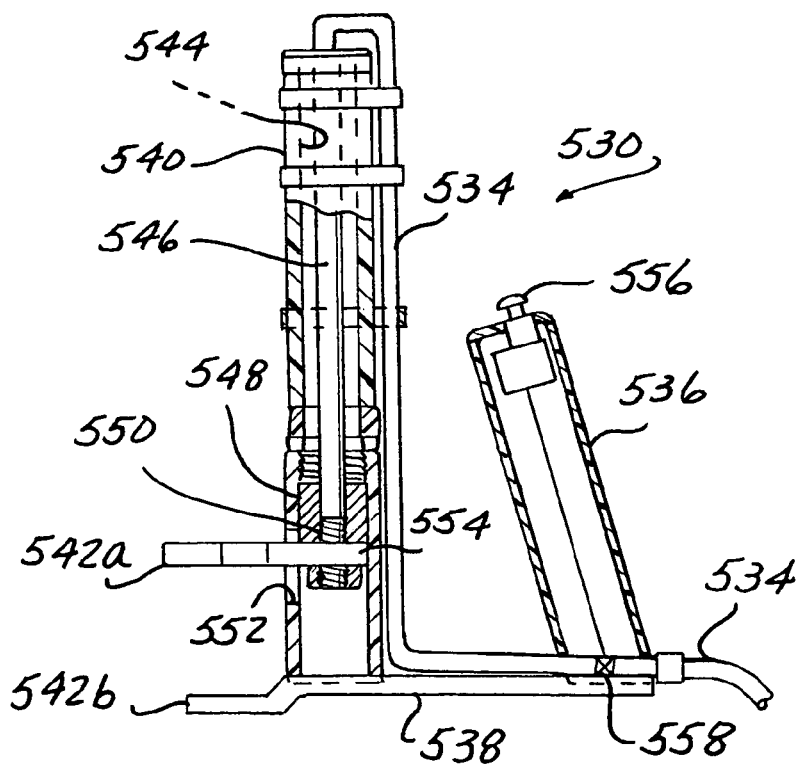
FIG. 46 is a sectional view of the pneumatically operated tool in FIG. 45 showing certain components.

A pneumatically operated tool 530 for assembling the barb clamp 10 is shown in FIGS. 45 and 46. The pneumatic tool 530 communicates with a source 532 of pressurized gas by a conduit 534. A handle 536 is connected to a base 538 at one end. The base 538 also has an air cylinder 540 connected thereto. The base 538 further has a lower jaw 542b, either integrally formed as part of the base 538 or connectable to one end of the base 538. The lower jaw 542b does not move during the assembly process.

The air cylinder 540 has a through bore 544 with a rod 546 having reciprocal movement therein. The rod 546 is held in place within the bore 544 by a bushing 548. The rod 546 is connected to a nut 550 which holds an extension 554 of an upper jaw 542a within the bore 544. The actual upper jaw 542a extends through a slot 552 outside of the bore 544. The upper jaw 542a is positioned directly above the lower jaw 542b. The upper jaw 542a has reciprocal movement limited by the opening of the slot 552. The upper jaw 542a moves with the movement of the rod 546. The upper jaw 542a may be integral with the extension 554 located in the bore 544 or connectable to the extension 544.

Conduit 534 extends from the source 532 of pressurized gas to the upper end of the bore 544 of cylinder 540. A normally closed valve 558 is selectively opened by an actuation button 556 on the handle 536. When the button 556 is depressed, the valve 558 opens to allow air flow from the source 532 into the bore 544 of the cylinder 540. The actuation button 556 may also include a pressure regulator of the compressed air to the air cylinder 540. The actuation button 556 and valve 558 are known and commonly used to regulate the flow and pressure of a fluid through a conduit.

When air pressure enters the bore 544, the pressure acts upon the rod 546 to move the rod 546 downwardly. As the rod 546 moves downwardly, the extension 554 integral with the upper jaw 542a carries the upper jaw 542a downwardly toward the lower jaw 542b. Although not shown in FIGS. 45 and 46, the upper and lower jaws 542a, b preferably have the configurations of one of the sets of jaws shown in FIGS. 42a-d to 44a-d to accurately assemble and lock the sleeve 20 over the collet 18.

To assemble and lock the sleeve 20 onto collet 18, the tube 14, with a fitting 12 and collet 18 thereon, is placed in the lower jaw 542b, so that the lower jaw 542b grips around the exterior surface of the collet 18. The sleeve 20 is positioned within an arcuate slot (similar to 524a in FIGS. 42a and b) of the upper jaw 542a, The actuation button 556 is depressed to allow flow from the pressurized air source 532 to the bore 544. The pressurized air will force the upper jaw 542a with the sleeve 20 therein downward so that the sleeve 20 slides over the collet 18 and locks into place. When the air pressure is removed from the air cylinder, the upper jaw 542a returns to its upward position as shown in FIG. 46. The pneumatically operated tool 530, as described, supra, provides the fastest and most accurate means to assemble the barb fitting 10.

Figure 48:
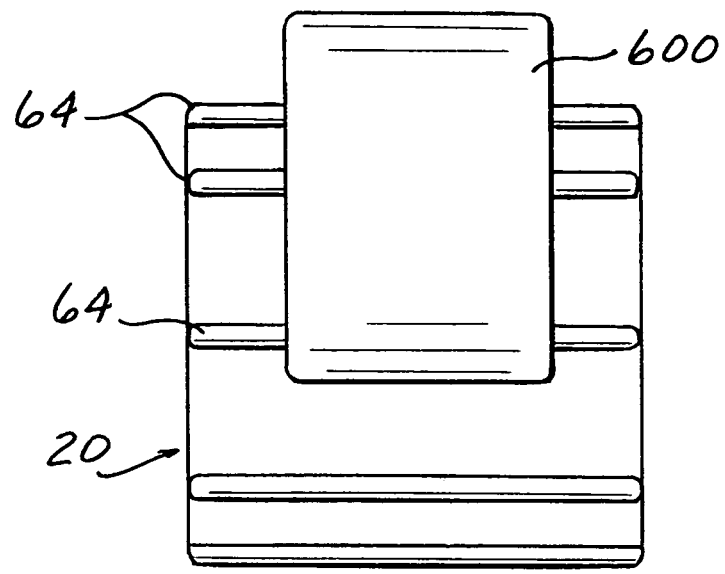
FIGS. 47-48 show a plastic spanner tool engaged with a sleeve.
Figure 47:
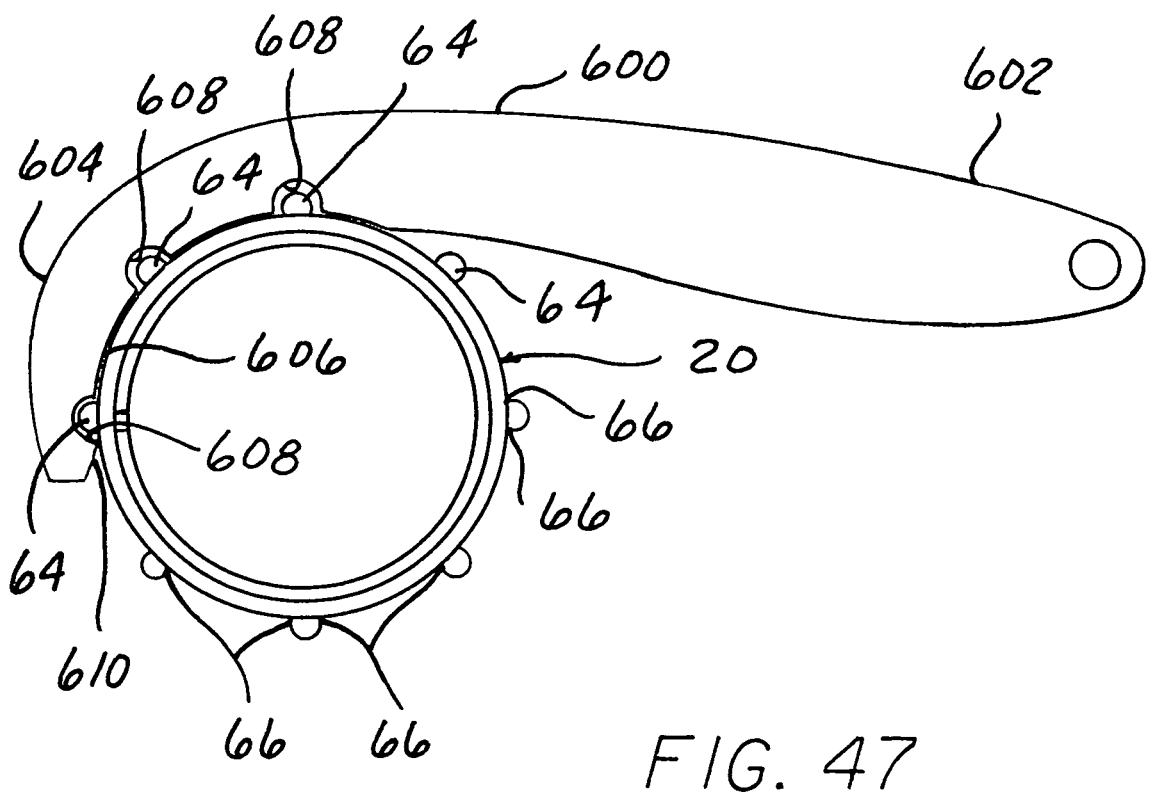

As discussed, supra, with regard to the ribbed sleeve as shown in FIGS. 21 and 22, a spanner tool 600 is provided (FIGS. 48, 47) to twist a sleeve 20 either onto or off of a collet. The spanner tool 600 has a handle 602 at one end and an arcuate formation 604 at the other end. The inside surface 606 of the arcuate portion or formation 604 has at least one, but preferably two or more, small arcuate cavities 608 sized and spaced to accommodate the size and spacing of the ribs 64 as discussed, supra, with respect to FIGS. 21 and 22. It is also preferred that at least the first arcuate cavity 608, which is spaced furthest from the handle, will have a forward edge that meets at a point 610 with the inside surface 606 of the arcuate portion 604. The point 610 is configured such that when the spanner tool 600 is implemented over the ribbed sleeve 20, the point 610 will grip into the concave surface 66 of the ribs 64 to adequately grip the sleeve 20.

To remove the sleeve 20 from the collet 18, another set of jaws 622a, 622b are retrofitted to the Robo Grip® tool 520 as shown in FIGS. 49a-49d. The upper jaws 622a has a hooked portion 624 with a cutting edge. The lower jaws 622b has a dished portion 626 for grasping one end of the sleeve 20. The modified Robo Grip® tool/pliers 520 have been configured to cut the sleeve allowing for the sleeve 20 to be peeled from the collet 18. The design allows for the safe removal of the barb clamp without damaging the tube 14 or fitting 12. The procedure to remove the sleeve 20 is as follows: Place the assembled barb clamp between the jaws 622a, 622b, making sure that the hooked portion 624 of the upper jaw 622a is sitting on the top of the sleeve 20. Ensure that the base of the sleeve 20 is sitting in the dished portion 626 of the lower jaw 622b. Close the tool/pliers 520 with a ratcheting motion (in some cases the sleeve will split). When the pliers 520 are fully closed, the sleeve 20 should be grasped on the sides of the sleeve firmly. Twisting the pliers in a counter clockwise direction will completely separate the sleeve. Safely peel off the sleeve and remove the collet 18. The sleeve 20 should be disposed of in the proper manner.

FIGS. 50a and 50b show a pair of jaws 722a, 722b which also can be attached to a standard hand tool, such as a Robo Grip® tool for disassembling the sleeve 20 from the collet 18. The first jaw 722a is an arcuate member having an arcuate slot 724. Surrounding the arcuate slot 724 is an arcuate ledge 726. Spaced from the arcuate slot 724, an arcuate wall 728 extends perpendicularly from the ledge 726. The second jaw 722b also has a central arcuate slot 732 with an arcuate ledge 734 extending around the slot 732. A first arcuate wall 736 extends perpendicularly from the ledge 734 and spaced from the arcuate slot 732. A second wall 738 extends perpendicular from a portion of the ledge 734 adjacent to the arcuate slot 732. The second wall 738 has the same height as the first arcuate wall 736. The second wall 738 has a thickness of approximately the thickness of a collet 18. The second wall 738 is spaced from the first arcuate 736 wall a distance greater than the thickness of a sleeve 20 to form a recess 740 therebetween.

The arcuate slot 724 and the arcuate ledge 726 of the first jaw 722 are configured and sized so that a portion of the sleeve rests on the ledge 7216. As the second jaw 730 meets the barb clamp 10, the second wall 736 contacts the collet 18. With further pressure on the jaws 722a, 722b, the second wall 736 of the second jaws 722b forces the collet through the arcuate slot 724 of the first jaw 722a and a portion of the sleeve into the recess 740. Only a portion of the collet 18 needs to be pushed or moved from the sleeve 20 to unlock the annular ring 48 from the annular groove 26.

The barb clamp of the present invention offers superior sealing features over the prior art. The barb clamp provides full 360° compression seal over the barb 16 and a full radial crimp via the tangs 28 behind the bard 16. Further, a full 360° compression is provided along the entire axial length of the barb fitting 12. In addition, the barb clamp has the attribute of resealing itself if the clamp is subject to pressure spike beyond the removed ultimate pressure tolerance because the collet is under compressor from a sleeve made of elastic material.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A barb clamp for connecting a device and a tube with a barb fitting having a first end attachable to the device and a second end insertable into the tube, said barb clamp comprising:

a single integral device having a collet portion and a sleeve portion, the sleeve portion defined by an upper elongate portion and said collet portion defined by a lower elongate portion, wherein the upper and lower elongate portions meet and are integrally joined along a common axis boundary, the sleeve portion having first and second opposing ends with first locking means thereon for locking the first end of the sleeve portion to the second end of the sleeve portion around the barb fitting and tube, and the collet portion having first and second opposing ends with second locking means thereon for locking the first end of the collet portion to the second end of the collet portion around the barb fitting and tube, wherein the upper elongate portion is offset from the lower elongate portion for overlapping a gap formed when winding around the barb fitting, and wherein the first locking means of the upper portion has a first tab extending from the first end of the sleeve portion, said first tab having exposed teeth traversing the width of the first tab and said first locking means having a first pocket formed in the second end with complementary teeth therein, said first pocket configured for receiving, encapsulating, and securing said first tab, wherein the second locking means of the lower portion has a second tab with exposed teeth extending from the second end of the collet portion at an opposing end from the first tab, and a second pocket having complementary teeth therein formed at the first end of the lower portion for receiving, encapsulating, and securing said second tab of the lower portion, and wherein the second pocket formed in the lower portion abuts the common axis boundary and the upper portion is disposed between the first tab and the first pocket.

2. A barb clamp for connecting a device and a tube with a barb fitting having a first end attachable to the device and a second end insertable into the tube, said barb clamp comprising:

a single integral device having a collet portion and a sleeve portion, the sleeve portion defined by an upper elongate portion and said collet portion defined by a lower elongate portion, wherein the upper and lower elongate portions meet and are integrally joined along a common axis boundary, the sleeve portion having first and second opposing ends with first locking means thereon for locking the first end of the sleeve portion to the second end of the sleeve portion around the barb fitting and tube, and the collet portion having first and second opposing ends with second locking means thereon for locking the first end of the collet portion to the second end of the collet portion around the barb fitting and tube, wherein the upper elongate portion is offset from the lower elongate portion for overlapping a gap formed when winding around the barb fitting, and wherein the first locking means of the upper portion has a first tab extending from the first end of the sleeve portion, said first tab having exposed teeth traversing the width of the first tab and said first locking means having a first pocket formed in the second end with complementary teeth therein, said first pocket configured for receiving, encapsulating, and securing said first tab, wherein the lower portion has an interior surface having a linear shelf formed thereon and extending the axial length of the collet portion between the second tab and second pocket for gripping a portion of the barb fitting.

3. The barb clamp of claim 1 wherein the first and second pockets have lateral edges terminating at the common axis boundary.

4. A barb clamp for connecting a device and a tube with a barb fitting having a first end attachable to the device and a second end insertable into the tube, said barb clamp comprising:

a single integral molded device having an elongate configuration for winding around the barb fitting in a sealing formation, said single integral device having an upper rectangular portion defining a sleeve portion and a lower rectangular portion defining a collet portion, said upper and lower rectangular portions sharing a common axis boundary and said upper rectangular portion offset from the lower rectangular portion for overlapping a gap formed around the barb fitting when the barb clamp is in an installed condition, said upper rectangular portion having first locking means for locking a first end of the upper rectangular portion to a second distal end of the upper rectangular portion and the lower rectangular portion having a second locking means for locking a first end of the lower rectangular portion to a second distal end of the lower rectangular portion, wherein at least one portion of the first and second locking means abuts the common axis boundary, wherein the first locking means includes a first tab extending from one end of the upper rectangular portion, said first tab having exposed teeth traversing the width of the first tab, and the second end of the upper rectangular portion having a first pocket formed therein having an interior surface with complementary teeth formed thereon for receiving, encapsulating and securing the first tab.

5. The barb clamp of claim 4 wherein the second locking means includes a second tab extending from the first end of the lower rectangular portion, said second tab having exposed teeth traversing the width of the second tab, and the second end of the lower rectangular portion having a second pocket formed therein having an interior surface with complementary teeth formed thereon for receiving, encapsulating and securing the second tab, and wherein the second pocket abuts the common axis boundary.

6. The barb clamp of claim 5 wherein an inner surface of the single integral device has a linear projection extending from the second tab to the second pocket for gripping into a barb on the barb fitting when the barb clamp is an installed condition around the barb fitting.

* * * * *

UNITED STATES PATENT AND TRADEMARK OFFICE
CERTIFICATE OF CORRECTION

PATENT NO.         : 7,357,425 B2
APPLICATION NO. : 10/918240
DATED                 : April 15, 2008
INVENTOR(S)       : Albert A. Werth It is certified that error appears in the above-identified patent and that said Letters Patent is hereby corrected as shown below:

On the Title Page Item (73), Line 1; Delete "Twins" and insert -- Twin --, therefor.

Column 2, Line 18; Delete "an" and insert -- a --, therefor.

Column 2, Line 23; Delete "an" and insert -- a --, therefor.

Column 12, Line 57; Delete "522a," and insert -- 522a.. --, therefor.

Column 13, Line 39; Delete "542a," and insert -- 542a.. --, therefor.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,357,425 B2 |
| APPLICATION NO. | : 10/918240 |
| DATED | : April 15, 2008 |
| INVENTOR(S) | : Albert A. Werth |

Page 1 of 1

It is certified that error appears in the above-identified patent and that said Letters Patent is hereby corrected as shown below:

Column 2, Line 18; Delete "an" and insert -- a --, therefor.
Column 2, Line 23; Delete "an" and insert -- a --, therefor.

Signed and Sealed this

Twenty-ninth Day of July, 2008

JON W. DUDAS
*Director of the United States Patent and Trademark Office*